US009959621B2

United States Patent
Hsu et al.

(10) Patent No.: US 9,959,621 B2
(45) Date of Patent: May 1, 2018

(54) TESTING APPARATUS WITH DUAL CAMERAS

(71) Applicant: Bonraybio Co., Ltd., Taichung (TW)

(72) Inventors: Cheng-Teng Hsu, Taichung (TW);
Hsuan-Yu Huang, Taichung (TW);
Chih-Pin Chang, Taichung (TW);
Kuang-Li Huang, Taichung (TW);
Yu-Chiao Chi, Taichung (TW)

(73) Assignee: Bonraybio Co., Ltd., Taichung (TW)

( * ) Notice: Subject to any disclaimer, the term of this patent is extended or adjusted under 35 U.S.C. 154(b) by 0 days. days.

(21) Appl. No.: 15/603,783

(22) Filed: May 24, 2017

(65) Prior Publication Data

US 2017/0330321 A1 Nov. 16, 2017

Related U.S. Application Data

(63) Continuation-in-part of application No. 15/345,061, filed on Nov. 7, 2016, and a continuation-in-part of application No. 15/152,470, filed on May 11, 2016.

(51) Int. Cl.
*G01N 15/06* (2006.01)
*G06T 7/00* (2017.01)
(Continued)

(52) U.S. Cl.
CPC ........... *G06T 7/0012* (2013.01); *G01N 15/06* (2013.01); *G01N 15/1429* (2013.01);
(Continued)

(58) Field of Classification Search
None
See application file for complete search history.

(56) References Cited

U.S. PATENT DOCUMENTS 3,656,840 A 4/1972 Smith et al.
5,021,651 A 6/1991 Ishikawa
(Continued)

FOREIGN PATENT DOCUMENTS

CN 2269833 Y 12/1997
CN 201535752 U 7/2010
(Continued)

OTHER PUBLICATIONS

International Search Report and Written Opinion dated Sep. 8, 2017 in International Application No. PCT/US17/32086.
(Continued)

*Primary Examiner* — Eileen Adams
(74) *Attorney, Agent, or Firm* — Perkins Coie LLP; Han-Wei Chen; Viola T. Kung

(57) ABSTRACT

Embodiments disclose a device for testing biological specimen. The device includes a sample carrier and a detachable cover. The sample carrier includes a specimen holding area. The detachable cover is placed on top of the specimen holding area. The detachable cover includes a magnifying component configured to align with the specimen holding area. The focal length of the magnifying component is from 0.1 mm to 8.5 mm. The magnifying component has a linear magnification ratio of at least 1. Some embodiments further include a multi-camera configuration. These embodiments include a first camera module and a second camera module arranged to capture one or more images of the first holding area and the second holding area, respectively. The processor may perform different analytic processes on the captured images of different holding areas to determine an outcome with regard to the biological specimen.

33 Claims, 35 Drawing Sheets

(51) Int. Cl.

| | |
|---|---|
| *G01N 21/80* | (2006.01) |
| *G01N 15/14* | (2006.01) |
| *H04N 7/18* | (2006.01) |
| *H04N 5/225* | (2006.01) |
| *G02B 21/36* | (2006.01) |
| *G02B 21/14* | (2006.01) |
| *G02B 21/24* | (2006.01) |

(52) U.S. Cl.
CPC .............. *G01N 21/80* (2013.01); *G02B 21/14* (2013.01); *G02B 21/244* (2013.01); *G02B 21/365* (2013.01); *H04N 5/2257* (2013.01); *H04N 7/181* (2013.01)

(56) References Cited

U.S. PATENT DOCUMENTS

| | | | |
|---|---|---|---|
| 5,267,087 | A | 11/1993 | Weidemann |
| 5,280,389 | A | 1/1994 | Kunikane et al. |
| 5,572,370 | A | 11/1996 | Cho |
| 5,894,346 | A | 4/1999 | Gu-Pin et al. |
| 8,460,942 | B2 | 6/2013 | Kislev et al. |
| 8,916,390 | B2 | 12/2014 | Ozcan et al. |
| 9,322,767 | B2 | 4/2016 | Ehrenkranz |
| 2002/0044347 | A1 | 4/2002 | Steenblik |
| 2002/0048819 | A1 | 4/2002 | Alley |
| 2004/0263810 | A1 | 12/2004 | Kirchner et al. |
| 2009/0251751 | A1 | 10/2009 | Kuhlmann |
| 2012/0148141 | A1 | 6/2012 | Ozcan et al. |
| 2013/0273524 | A1 | 10/2013 | Ehrenkranz |
| 2014/0254004 | A1 | 9/2014 | Wooder et al. |
| 2014/0273188 | A1 | 9/2014 | Mohan et al. |
| 2015/0035966 | A1 | 2/2015 | Salsman |
| 2015/0036131 | A1 | 2/2015 | Salsman |
| 2015/0204891 | A1 | 7/2015 | Parsons |
| 2015/0276736 | A1 | 10/2015 | Boilard et al. |
| 2015/0287570 | A1 | 10/2015 | Hayashi et al. |
| 2015/0338387 | A1 | 11/2015 | Ehrenkranz |
| 2016/0004057 | A1 | 1/2016 | Lin et al. |
| 2016/0131573 | A1 | 5/2016 | Lu |
| 2017/0109879 | A1 | 4/2017 | Urbano et al. |

FOREIGN PATENT DOCUMENTS

| | | |
|---|---|---|
| CN | 202083642 U | 12/2011 |
| CN | 101952762 B | 11/2012 |
| CN | 202974876 U | 6/2013 |
| CN | 102236011 B | 10/2013 |
| CN | 203232198 U | 10/2013 |
| CN | 203688559 U | 7/2014 |
| TW | M491168 U | 12/2014 |
| TW | M491840 U | 12/2014 |
| WO | 2009/053927 A2 | 4/2009 |
| WO | 2014/099629 A1 | 6/2014 |
| WO | 2015/020884 A1 | 2/2015 |
| WO | 2015087232 A1 | 6/2015 |

OTHER PUBLICATIONS

European Search Report dated Oct. 16, 2017 in European Application No. EP17170716.

Zhou et al., "The Semen pH Affects Sperm Motility and Capacitation", PLOS ONE, vol. 10, No. 7, Jul. 14, 2015, pp. 1-15.

TESTING APPARATUS WITH DUAL CAMERAS

This application is a continuation-in-part of U.S. application Ser. No. 15/345,061, filed Nov. 7, 2016; which is a continuation-in-part of U.S. application Ser. No. 15/152,470, filed May 11, 2016; the contents of both applications are incorporated herein by reference in their entireties.

FIELD OF THE INVENTION

The invention relates to equipment for testing biological specimen, and relates particularly to testing equipment with a magnifying function or an analyte quantification function.

BACKGROUND OF THE INVENTION

Currently, testing of liquid contents, are typically consigned to professional testing authorities for performing testing using expensive microscope equipment with high magnification ratios. Since an individual does not have microscope equipment, the testing activity cannot be performed by the individual.

However, in some testing categories nowadays testing is required to be performed on a regular basis; therefore the need for frequent testing poses an excessive burden in terms of time and expense. For example, the category of long term testing includes semen testing for patients with infertility issues. The semen testing is mainly directed to performing observations on the number of sperms, their motility and morphology.

The semen testing method involves resting semen of a male subject at a room temperature for a period of time, and taking a drop of the sample and instilling the sample to a slide, and observing the sample under a microscope. The observations not only include performing high magnification observation of individual sperm to identify the external appearance of individual sperm, but also include performing observations of overall sperms in a large quantity, their motility, morphology and the quantity per unit area. However, an individual cannot perform the semen testing by himself because the industry have not yet developed a technology that allows an individual to perform testing through a simple aiding device.

SUMMARY OF THE INVENTION

The invention provides a testing equipment with magnifying function, which is significantly less expensive than conventional testing equipment, requires less labor for testing, and is easy to use. The technology can be applied to semen testing, as well as other testing areas such as microorganisms in water, water quality, blood, urine, body fluid, stool, and skin epidermis tissues/cells. The technology provides a simple testing product with significantly lower usage cost than convention techniques using laboratory microscope equipment.

Comparing to the conventional techniques, the testing equipment with magnifying function disclosed herein provides a simple structure that can significantly lower the cost of specimen magnifying testing structure, for tests such as sperm test, urinalysis or other body fluid analysis. The technology disclosed herein can be used in a wide range of applications, through the design of the carrier having the specimen holding area, the magnifying part and the unique innovative configuration. For example, the testing equipment with magnifying function can be applied to inspect the counts, the motility and the morphology of sperm specimen.

The testing equipment with magnifying function of the invention is suitable for performing tests at home. The results of the test can be obtained instantly and the cost is low. For example, the testing equipment with magnifying function provides a way to assess male fertility at home for couples seeking pregnancy so that the couples can make an informed decision whether medical intervention is needed.

The disclosed technology can be conveniently integrated with existing intelligent communications device (such as smart phone or tablet), and enables the use of existing intelligent communications device to capture magnified testing images and perform subsequent operations such as storing and transferring the images. The cost of the devices is low so that the devices can be implemented as disposable devices or reusable devices.

At least some embodiments of the present invention are directed to a device (e.g., a test cartridge or a test strip) for testing biological specimen. The device includes a sample carrier and a detachable cover. The sample carrier includes a specimen holding area. The detachable cover is placed on top of the specimen holding area. The detachable cover includes a magnifying component configured to align with the specimen holding area. The focal length of the magnifying component is from 0.1 mm to 8.5 mm. The magnifying component has a linear magnification ratio of at least 1.0.

At least some embodiments of the present invention are directed to a system for testing biological specimen. The system includes the device for testing biological specimen mentioned above and a base component. The base component includes an insertion port for inserting the device for testing biological specimen into the base component. The base component further includes a camera component for capturing the image of the specimen holding area, or a form-fitting frame for securing a mobile device that includes a camera component for capturing the image of the specimen holding area. The base component can further include a supplemental lens placed below the camera component. A combination of the magnifying component and the supplemental lens can have an effective linear magnification ratio of at least 1.0.

At least some embodiments of the present invention are directed to a method for testing sperms using the device for testing biological specimen. The method includes steps of: obtaining the device for testing biological specimen mentioned above, applying a sperm specimen to the specimen holding area, recording a video or an image of the sperm specimen; determining the sperm count of the sperm specimen based on the at least one frame of the recorded video or the recorded image; and determining the sperm motility of the sperm specimen based on the recorded video or the recorded image.

At least some embodiments of the present invention are directed to a system for testing biological specimen. The system includes a disposable device for testing biological specimen and a base component. The disposable device includes a sample carrier including a specimen holding area and a detachable cover placed on top of the specimen holding area. The base component includes an insertion port for inserting the disposable device into the base component and a camera. The camera, which includes an image sensor and an optical lens module, captures one or more image(s) of the specimen holding area.

Some embodiments of the present disclosure include an apparatus for testing biological specimen. The apparatus can include a casing that has an opening. A receiving mechanism can receive a carrier inserted through said opening. The carrier can include a first holding area and a second holding area. The first and second holding areas may carry or have been exposed to the biological specimen.

The apparatus, in some implementations, can include two camera modules. Among the camera modules is a first camera module arranged to capture one or more images of the first holding area, and a second camera module arranged to capture one or more images of the second holding area. Further, some embodiments include a main circuit board carrying a processor that is configured to perform a first analytic process on the captured images of the first holding area. The processor may be configured to perform a second analytic process different from the first analytic process on the captured images of the second holding area. In some embodiments, the processor can determine an outcome with regard to the biological specimen based on results from both the first and the second analytic processes. In accordance with one or more embodiments, said receiving mechanism, said first and second camera modules, and said main circuit board are all enclosed within the casing.

Moreover, in some embodiments, when the processor identifies the first holding area being in a first shape, the processor is configured to perform a certain analytic process. For example, if the first shape represents that the biological specimen includes sperm from a male subject, then the process can determine one or more properties of the sperm. The properties can be determined may include: a concentration of the sperm, a motility of the sperm, and/or a morphology of the sperm. The determination of the one or more properties of the sperm may be performed, in some examples, by using the second camera module. In some of these examples, the processor is further to determine at least one additional property of the sperm by using the first camera module. This additional property may include an acidity of the sperm. For example, the carrier can include a pH indicator in the first holding area to represent the acidity of the sperm with colors, and the processor can recognize the colors for identifying the acidity.

In some examples, when the processor identifies the first holding area being in a second shape, which may indicate that the biological specimen includes urine from a female subject, the processor is configured to determine one or more properties of the urine. The properties can be determined can include: an LH level, an FSH level, and/or an HCG level. Like acidity, the determination of the one or more properties of the urine may be performed by using the first camera module. Similarly, the carrier can include an LH indicator, an FSH indicator, and/or an HCG indicator in the first holding area.

In some embodiments, the first camera module has a lower magnifying ratio and/or a lower camera resolution than the second camera module.

In some embodiments, the processor can be configured to (1) utilize the first camera module to identify a shape of the first holding area on the carrier; and (2) select, based on the shape of the first holding area, a set of analytic processes to be performed. The shape of the first holding area can identify a gender information of the biological specimen. Then, in response to the shape of the first holding area being a first shape, the set of analytic processes selected by the processor can determine a fertility with regard to reproductive cells of a first gender. Further, in response to the shape of the first holding area being a second shape, the set of analytic processes selected by the processor can determine a fertility with regard to reproductive cells of a second gender.

Reference will now be made in detail to the present preferred embodiments of the invention, examples of which are illustrated in the accompanying drawings.

DESCRIPTION OF THE EMBODIMENTS

Figure 1A:
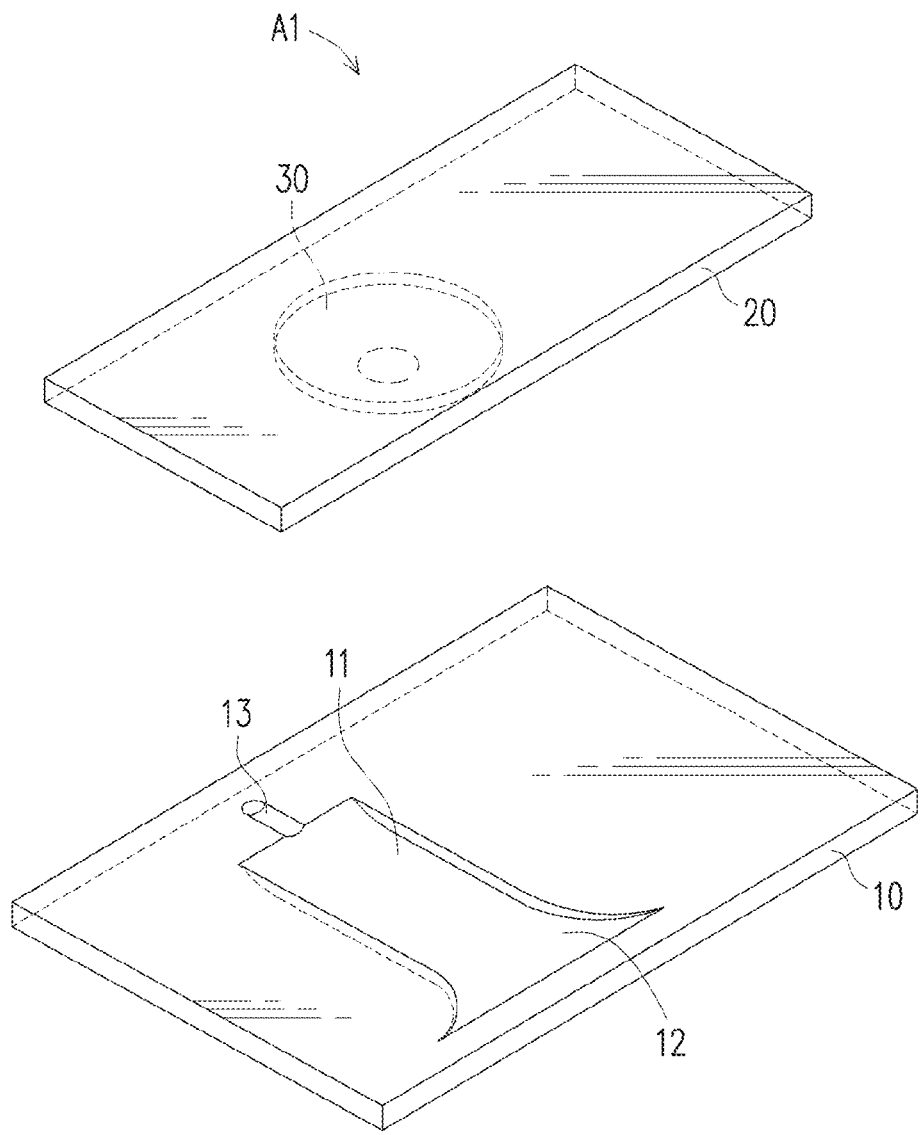
FIG. 1A is an exploded view of a testing equipment with magnifying function according to an embodiment of the invention.
Figure 1B:
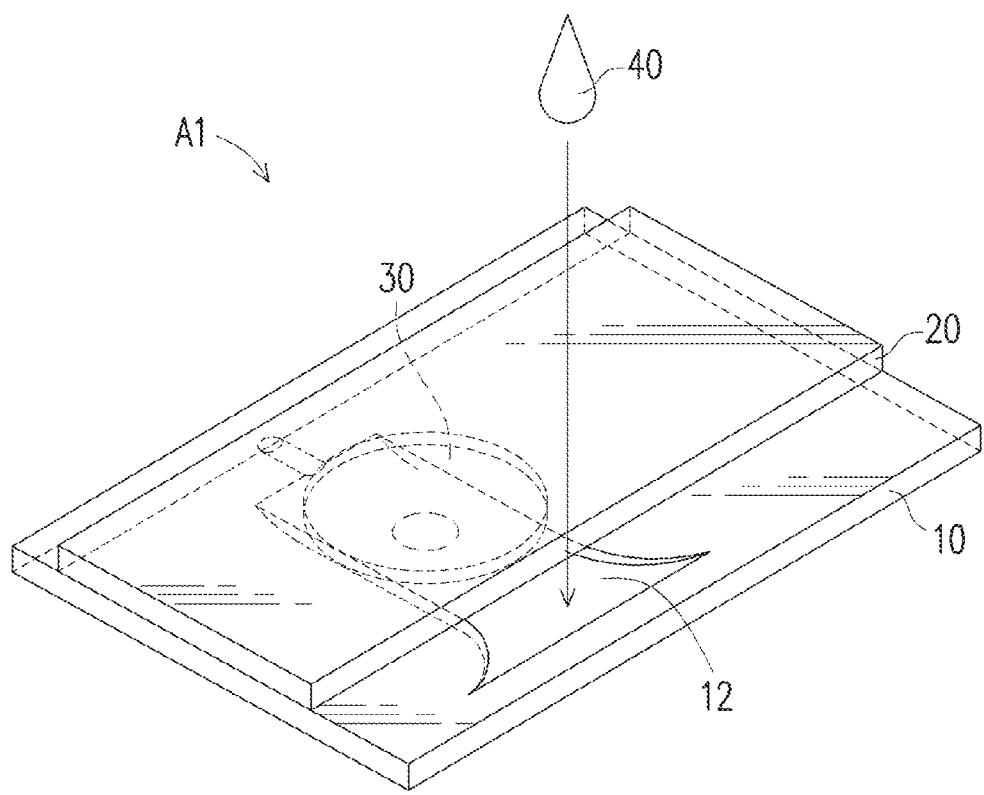
FIG. 1B is an assembled view of the testing equipment of FIG. 1A.

FIGS. 1A and 1B illustrate a testing equipment with magnifying function according to an embodiment of the invention. Embodiments disclosed herein are used for illustration purpose and should not be construed as required limitation to the invention. The testing equipment with magnifying function A1 includes: a carrier 10 having a specimen holding area 11 formed on top of the carrier 10, a cover 20 stacked on top of the carrier 10, and at least one magnifying part 30 (also referred to as magnifying component or magnifier) including a convex lens type surface formed on the cover 20.

The magnifying part 30 of the present embodiment includes a planar convex lens as illustrated in FIG. 1A. However, other type of magnifying lens, e.g., a dual-sided lenticular lens can be included as the magnifying part 30. The magnifying part 30 is disposed to be aligned with and to cover the specimen holding area 11 of the carrier 10. The magnifying part 30 may have various magnification ratios based on testing requirements of various tests. For example, the tests can include semen test, urine test, synovial joint fluid test, dermatological test, water test, or other body fluid tests, etc.

A test using the testing equipment A1 with magnifying function of the present embodiment does not require additional magnifying lens or laboratory microscopes, which are expensive and time-consuming to operate. Furthermore, there is no needed to align the specimen holding area with the magnifying lens or laboratory microscopes.

As illustrated in FIG. 1A, the specimen holding area 11 of the carrier 10 may be formed with a dented configuration. The dented configuration design provides a stable and large storage space containing a specimen 40. The dented configuration allows the specimen to rest for a required period of time before performing the testing. For example, before performing a motility testing on a semen specimen, it is necessary to rest the semen specimen in a room temperature for a required period of time before performing the motility testing.

The specimen 40 can be first instilled in the dented configuration, i.e., the specimen holding area 11 of the carrier 10 to rest for a period of time. As shown in FIG. 1B, a total area of the cover 20 can be smaller than a total area of the carrier 10. A specimen receiving port 12 exposed outside the cover 20 is formed on one side of the specimen holding area 11. The specimen receiving port 12 can be designed to have a shape expanding outwards, which can help smoothly instilling the specimen.

Figure 2A:
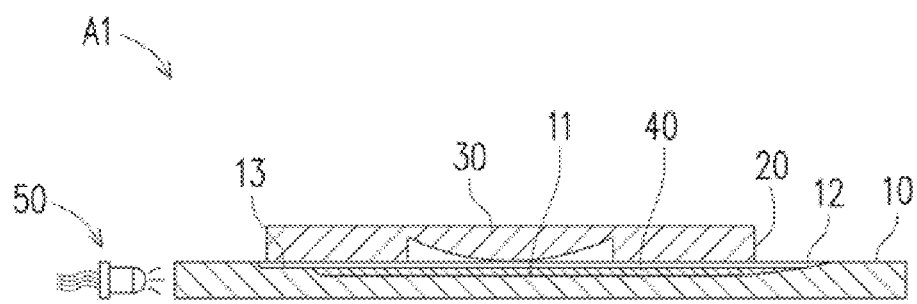
FIG. 2A is a cross-sectional view of the testing equipment of FIG. 1A.

FIG. 2A shows an air channel 13 that extends beyond the other side of the cover 20 and is formed on the other side of the specimen holding area 11. The air channel 13 may prevent air filling the inside of the specimen holding area 11, which prevent receiving of the specimen when the specimen is in a liquid status.

As shown in FIG. 2A, a lateral illumination device 50 can be disposed at one side of the carrier 20 of testing equipment A1. The lateral illumination device 50 can provide illumination for the specimen 40 in the specimen holding area 11 and therefore improve resolution of the captured testing images of the specimen 40. In some embodiments, the specimen holding area 11 can receive illustration from light source(s) on the top of or at the bottom of the testing equipment A1.

Figure 2B:
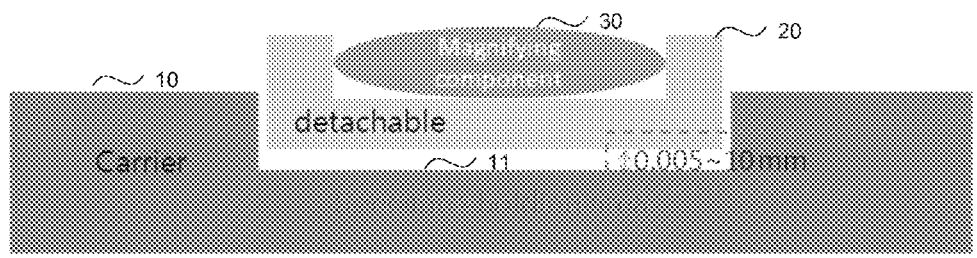
FIG. 2B is a cross-sectional view of another embodiment of testing equipment.

As illustrated in FIG. 1A, the magnifying part 30 and the cover 20 may be integrally formed, i.e., the magnifying part 30 and the cover 20 can be a single component. In other embodiments such as the embodiment illustrated in FIG. 2B, the detachable cover 20 and the magnifying component 30, which is disposed in the recess 21 of detachable cover 20, can each be separate components that are adapted to be integrated together. In other words, the same type of detachable cover 20 can be integrated with different magnifying components 30 of various magnification ratios.

In some embodiments, the distance between the bottom of the detachable cover 20 and the specimen holding area 11 is from 0.005 mm to 10 mm. In some embodiments, the distance between the bottom of the detachable cover 20 and the specimen holding area 11 is about 0.01 mm. The testing equipment can include one or more spacers (not shown) to ensure the distance between the bottom of the detachable cover 20 and the specimen holding area 11. The spacer(s) can integrally formed with the detachable cover 20 or the specimen holding area 11 of the carrier 10.

In some embodiments, the strip including the carrier 10 and the cover 20 is for sperm test. In some embodiments, the optimal angular magnification ratio for determining sperm concentration and motility is about 100 to 200. In some embodiments, the optimal angular magnification ratio for determining sperm morphology is about 200 to 300. The thinner the magnifying component, the higher the angular magnification ratio.

The focal length of the magnifying component can also relate to the angular magnification ratio. In some embodiments, a magnifying component with an angular magnification ratio of 100 has a focal length of 2.19 mm. A magnifying component with an angular magnification ratio of 156 has a focal length of 1.61 mm. A magnifying component with an angular magnification ratio of 300 has a focal length of 0.73 mm. In some embodiments, the magnifying component has an angular magnification ratio of at least 30, preferably at least 50. In some embodiments, the focal length of the magnifying component is from 0.1 mm to 3 mm.

Figure 3:
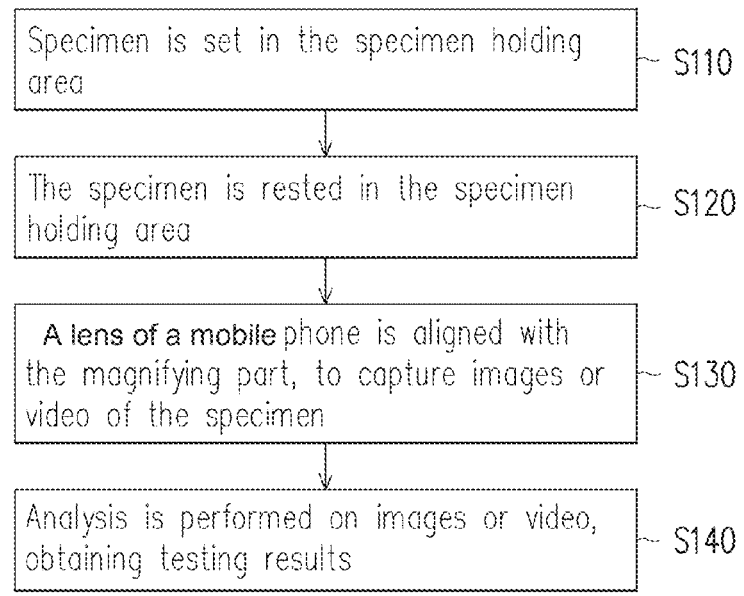
FIG. 3 is a flow diagram of testing for a testing equipment according to an embodiment of the invention.

FIG. 3 illustrates a sample process for performing testing using the testing equipment A1 with magnifying function illustrated in FIG. 1B. At step S110, the specimen 40 to be tested is set in the specimen holding area 11. At step S110, the cover 20 is stacked on top the carrier 10, before setting the specimen 40 to be tested in the specimen holding area 11 from the specimen receiving port 12. Alternatively, the specimen 40 to be tested can be set in the specimen holding area 11 directly first, before the cover 20 is stacked on top the carrier 10. At step S120, the specimen 40 is rested in the specimen holding area 11 selectively for a period of time according to testing requirements of the specimen 40. At step S130, an intelligent communication device (e.g., a mobile phone) is attached on the cover 20, and the camera of the mobile phone is aligned with the magnifying part 30, to use the camera of the mobile phone to capture a picture or video of the specimen through the magnifying part 30. At step S140, an application (APP) running at the mobile phone or other analysis device may be used to perform analysis of the picture or video, for obtain testing results.

Figure 4:
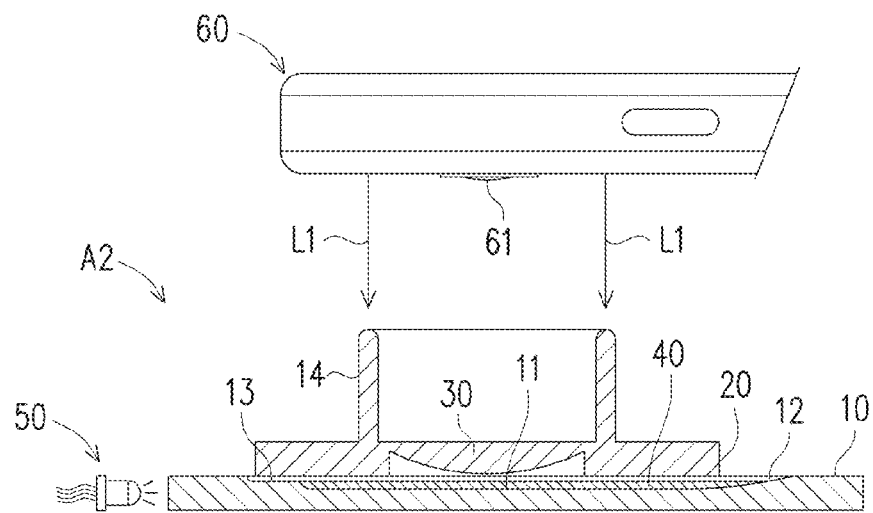
FIG. 4 is a cross-sectional view of a testing equipment with magnifying function according to another embodiment of the invention.

As illustrated in FIG. 4, a supporting side (such as a protruding part) 14 may further be formed on a top of the cover 20 of a testing equipment A2 at a border of the magnifying part 30. In some embodiments, the protruding type support structure may be formed on top of the cover 20 by the addition of the protruding part 14. When the user attempts to use an intelligent communications device 60 (e.g., a mobile device such as a smart phone or tablet) to capture the image or video of the specimen, a side of the intelligent communications device 60 having a camera 61 may be secured to the protruding part 14 (along the direction shown by the arrow L1). Thus, the testing equipment A2 allows the user to use the intelligent communications device 60 for capturing the image or video of the specimen, and does not require an expensive testing apparatus for recording the image or video. Furthermore, the height of the protruding part 14 can be pre-determined for a best observation distance based on specification of the camera 61 and the testing equipment A2.

Figure 5:
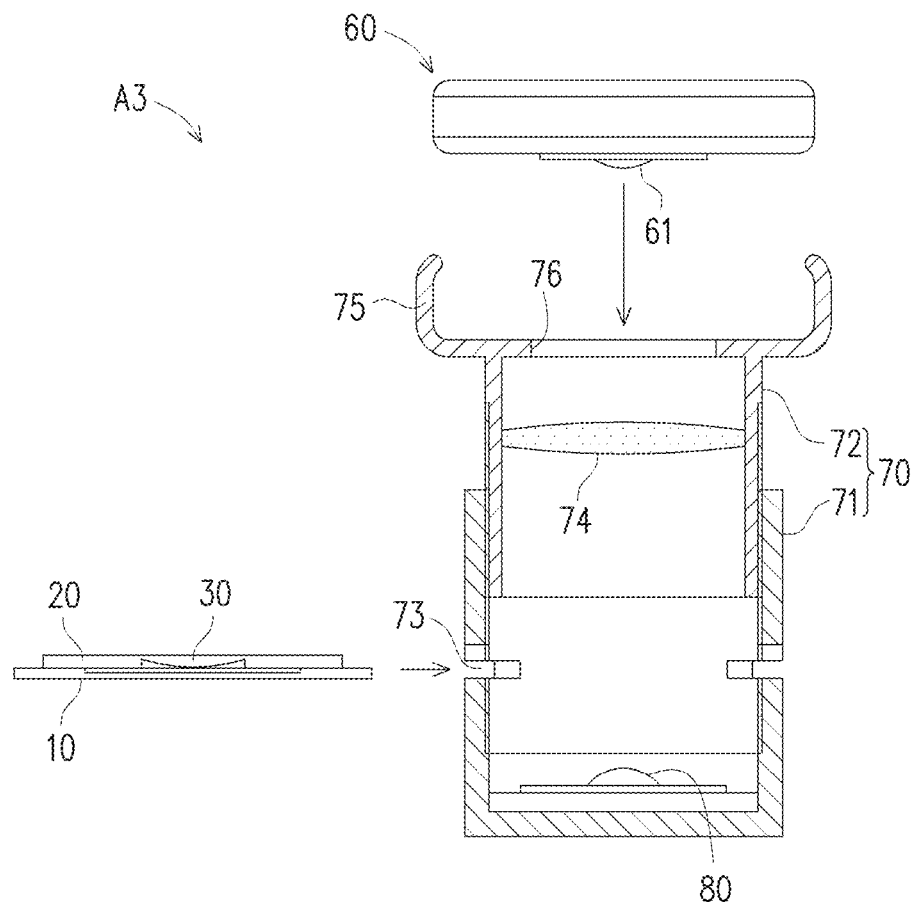
FIG. 5 is a cross-sectional view of a testing equipment with magnifying function according to another embodiment of the invention.
Figure 6:
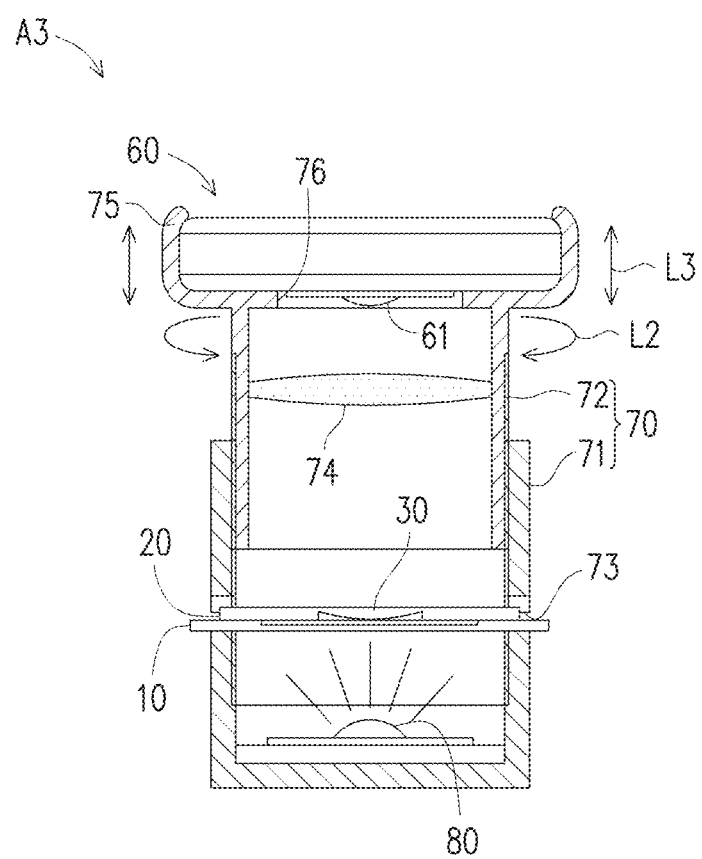
FIG. 6 is a schematic diagram of the testing equipment of FIG. 5 being used.

As shown in FIG. 5 and FIG. 6, a testing equipment A3 can include a barrel type base 70 (also referred to as base component). The barrel type base 70 includes a lower barrel base 71 and a upper barrel body 72 that can be lifted or descended with respect to the lower barrel base 71. The lower barrel base 71 has an insertion port 73 providing an insert position for the cover 20 and the carrier 10 stacked together. An upward lighting device 80 is disposed on a bottom part of the lower barrel base 71, to provide illumination to the combination of the cover 20 and carrier 10 from the bottom. The upper barrel body 72 can include, e.g., at least one additional magnification lens 74 for further magnification.

The upper barrel body 72 can be attached to the lower barrel base 71 using a screw thread mechanism such that the upper barrel body 72 that can be lifted or descended with respect to the lower barrel base 71 like a screw. In other words, the upper barrel body 72 can be rotated with respect to the lower barrel base 71 along the arrow L2 directions such that the upper barrel body 72 moves up and down along the arrow L3 directions with respect to the lower barrel base 71. By adjusting the height of the upper barrel body 72 with respect to the lower barrel base 71, the system adjusts the height of the magnification lens 74 (hen changing the magnification ratio) and the height of the camera 61.

An assembling frame 75 (also referred to as form-fitting frame) may be disposed at an upper end of the upper barrel body 72. The assembling frame 75 secures the intelligent communications device 60 at a pre-determined position. The assembling frame 75 has a camera alignment hole 76. The camera 61 of the intelligent communications device 60 can receive light from the specimen through the camera alignment hole 76.

The camera 61 disposed on current intelligent communications device 60 typically only have a digital zoom function. Generally an optical zoom lens is required for testing with a high accuracy. However, the user using the testing equipment A3 does not need a camera 61 having an optical zoom lens. The high adjustment function of the testing equipment A3 provides a flexible solution for aligning the specimen, the magnifying lens, and the camera 61.

FIG. 6 shows the intelligent communications device 60 that has been assembled and secured onto the assembling frame 75, which is disposed on the upper barrel body 72. The cover 20 and the carrier 10 containing the specimen 40 are inserted through the insertion port 73. The upward lighting device 80 may provide illumination to and increase the brightness of the specimen.

The upper barrel body 72 or the barrel type base 70 can rotated along the directions L2, to adjust the height of the magnification lens 74 and the camera 61 upwards or downwards along the directions L3. The height adjustment mechanism enables a function for adjusting the magnification ratio. The camera 61 may capture dynamic videos or static testing images of the specimen 40 after magnification. Furthermore, the intelligent communications device 60 can user its originally equipped functions to store the captured videos or images, to transfer the testing images or videos, and to conduct subsequent processing.

Figure 7:
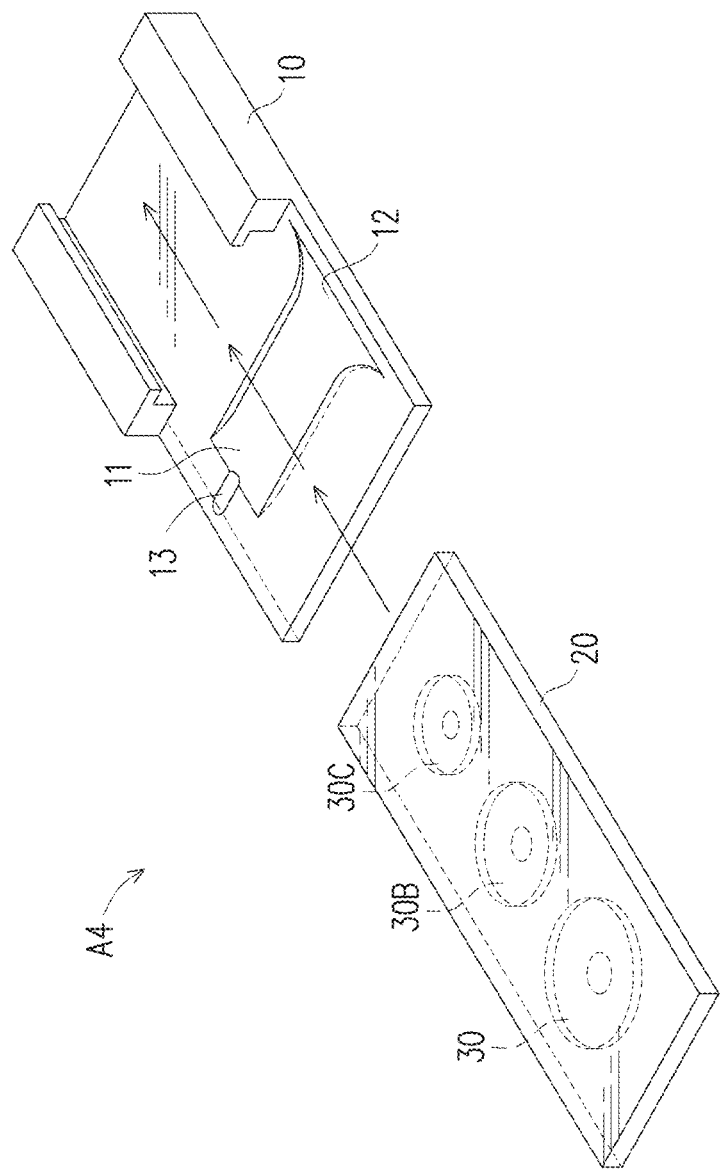
FIG. 7 is a schematic diagram of a testing equipment with magnifying function according to another embodiment of the invention.

As shown in FIG. 7, a testing equipment A4 with magnifying function includes a plurality of magnifying parts 30, 30B, 30C with different magnification ratios disposed on the cover 20. The user may shift the cover 20 to align the specimen holding area 11 of the carrier 10 with any of the magnifying parts 30, 30B, 30C with different magnification ratios, in order to obtaining testing results with different magnification ratios. By this design, the testing equipment A4 with magnifying function of a single module can be applied to satisfies magnification requirements of multiple testing protocols, without the need of changing the magnifying part or the cover.

Figure 8:
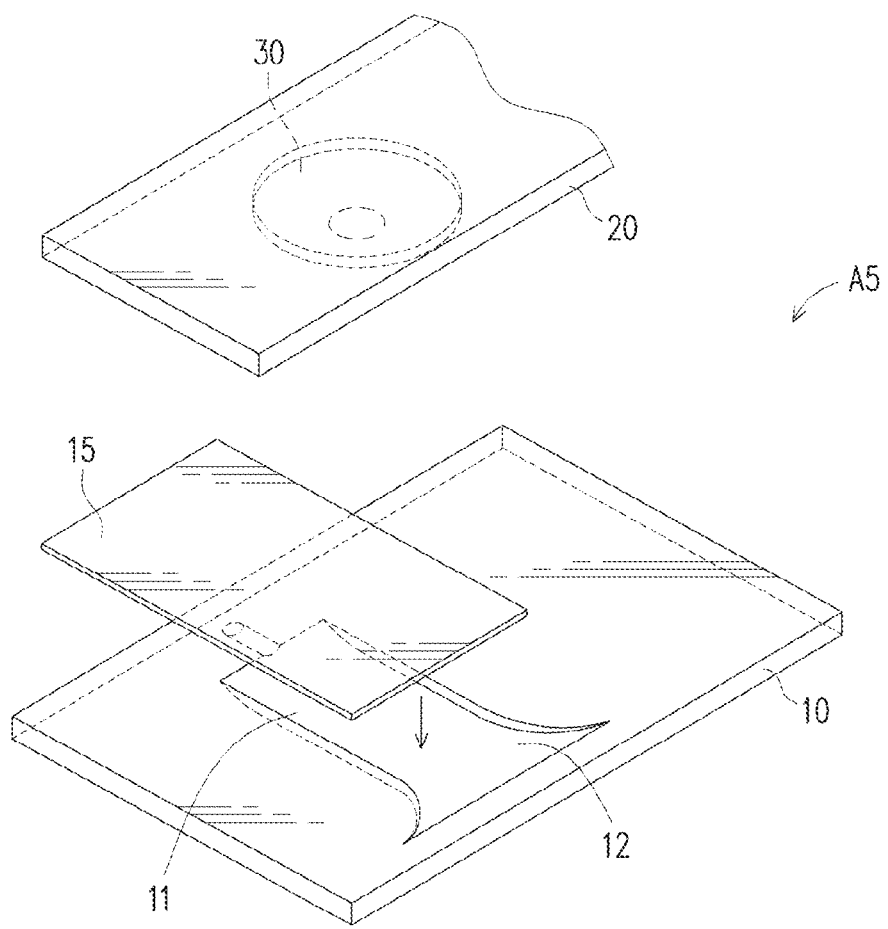
FIG. 8 is a schematic diagram of a testing equipment with magnifying function according to another embodiment of the invention.

As shown in FIG. 8, a testing equipment A5 with magnifying function includes a flexible transparent film 15. The flexible transparent film 15 is disposed between the carrier 10 and the magnifying part 30, and covers the specimen holding area 11. The flexible transparent film 15 covers the specimen 40 (in liquid state) such that the specimen 40 in a confined space. Thus, outside influences due to air, dust and dirt are confined to a minimum level. Furthermore, the testing equipment A5 may adjust the focal length by the varying the thickness of the flexible transparent film 15.

Figure 9:
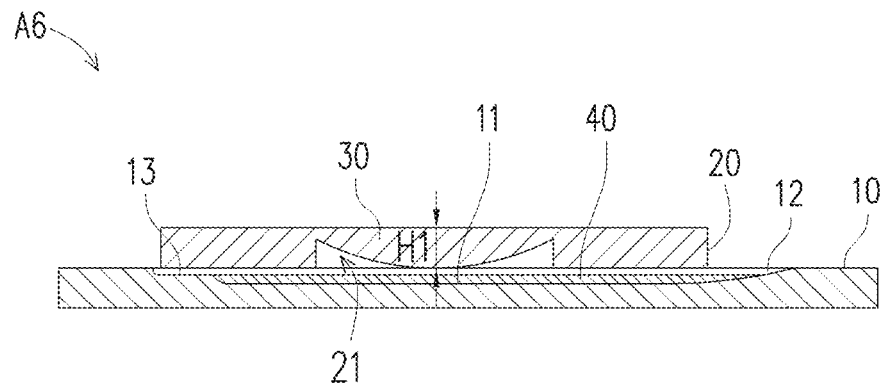
FIG. 9 is a schematic diagram of a testing equipment with magnifying function according to another embodiment of the invention.
Figure 10:
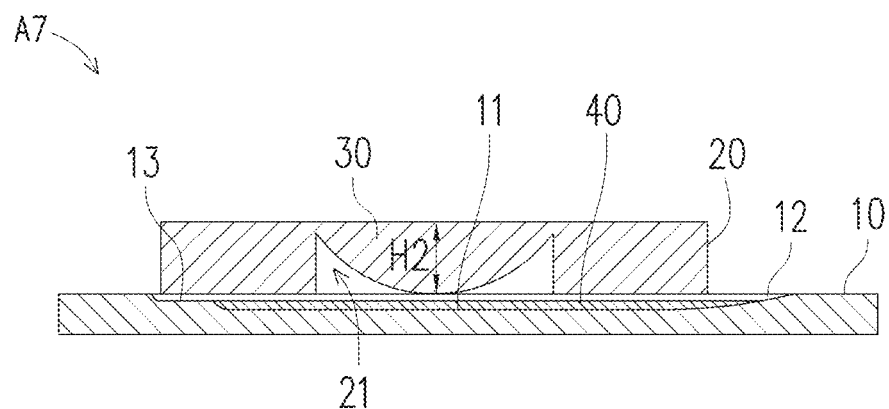
FIG. 10 is a schematic diagram of a testing equipment with magnifying function according to another embodiment of the invention.

As shown in FIG. 9, the magnifying part 30 of a testing equipment A6 with magnifying function is a planar convex lens, and a surface of the magnifying part 30 facing the carrier 10 is a protruding surface. Therefore, an upwardly concave type hollow part 21 is formed at the surface of the magnifying part 30 facing the carrier 10. A focal length parameter H1 is defined by the thickness of the thickest part of the magnifying part 30 of the planar convex lens. As shown in FIG. 10, a focal length parameter H2 of a testing equipment A7 with magnifying function is different than the focal length parameter H1 of FIG. 9.

The focal lengths H1 and H2 may be adjusted by changing thickness of the cover 20 or the size of the curvature of the magnifying part 30. For example, the focal length H2 shown in FIG. 10 is greater than the focal length H1 shown in FIG. 9, and is achieved by changing the size of the curvature of the magnifying part 30. In this way, testing requirements of various focal lengths may be satisfied by adopting different magnifying parts 30.

In some embodiments, the magnifying part 30 can be transparent and the rest of the cover 20 can be opaque. In addition, the carrier 10 may include the specimen holding area 11 which is transparent. The remaining of the carrier 10 can be opaque. When the testing operations are performed on the testing equipment, the light can propagate through the the specimen holding area 11, the magnifying part 30 such that chance of light interference in other parts of the device is suppressed.

Figure 11:
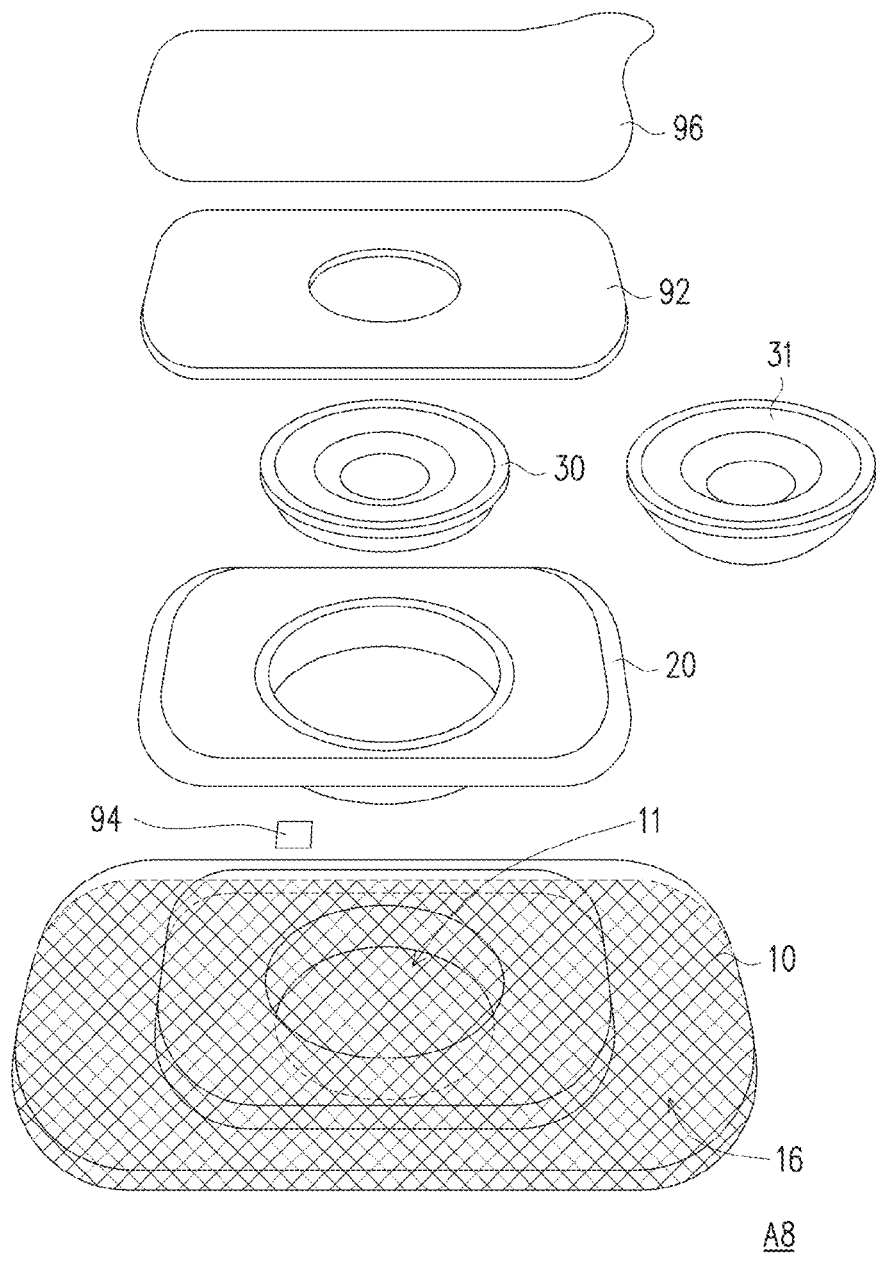
FIGS. 11-13 are views of testing equipment with magnifying function according to another three embodiments of the invention.

Referring to FIG. 11, in a testing equipment A8 with magnifying function, the carrier 10 of the testing equipment A8 further includes a light beam auxiliary guiding structure 16 formed at the bottom surface of the carrier 10. The carrier 10 can be made of transparent or translucent material. The light beam auxiliary guiding structure 16 can be opaque or include a granular structure, a rough pattern, an engraved pattern, or other suitable structure that scatters the light beam reaching the guiding structure 16. The light beam auxiliary guiding structure 16 may provide a particular pattern for the entire surface or a partial surface of the cover and the carrier. The light beam auxiliary guiding structure 16 may also be formed all around the side surfaces of the carrier 10.

When the cover 20 and the carrier 10 are stacked and are attached to the intelligent communications device 60 (as illustrated in FIG. 4 for example), the magnifying part 30 is aligned with the camera 61 of the intelligent communications device 60. In addition, a fill light (not shown) can be disposed near the camera 61 on surfaces of the intelligent communications device 60. The light beam provided by the fill light may be guided to the carrier 10 to illuminate the specimen holding area 11 through the cover 20. At the same time, the light beam auxiliary guiding structure 16 of the carrier 10 may cause the light beam provided by the fill light to scatter, further improving the brightness and illumination uniformity of the specimen holding area 11.

By disposing the light beam auxiliary guiding structure 16, the testing equipment does not require an additional fill light source to illuminate the carrier 10. Therefore, cover 20 includes a light-transmissive material so that the fill light from of the intelligent communications device 60 can reach the specimen through the cover 20. In some alternative embodiments, the device does not include a cover 20 and the fill light directly reach the carrier 10 without propagating through the cover 20.

The testing equipment A8 with magnifying function can include a non-slip film 92 and a pH test paper 94. The non-slip film 92 is attached on the supporting side (such as the top side) of the cover 20, and is used to stably dispose the cover 20 to the camera 61 of the intelligent communications device 60, as shown in FIG. 4, such that the magnifying part 30 is aligned to the camera 61 of the intelligent communications device 60. Using the non-slip film 92, the positioning of the intelligent communications device 60 relative to the testing equipment A8 is secured to a pre-determined configuration.

The non-slip film 92 can have an opening aligned to the magnifying part 30, so that the non-slip film 92 does not block the light transmitted from the specimen through the magnifying part 30 to the camera 61. The non-slip film 92 can include a material of, for example, silicon. The pH test paper 94 can be disposed on the specimen holding area 11 of the carrier 10, to provide an indication of the pH value of the specimen. The pH test paper 94 may be replaced after the usage.

In addition, the magnifying part 30 and the cover 20 can adopt a detachable design. Thus, the user may select another magnifying part 31 different from the magnifying part 30 to replace the original magnifying part 30 based on testing requirements. Various magnifying part can be assembled with the cover 20 are assembled to achieve different magnification ratios or other optical features.

Figure 12:
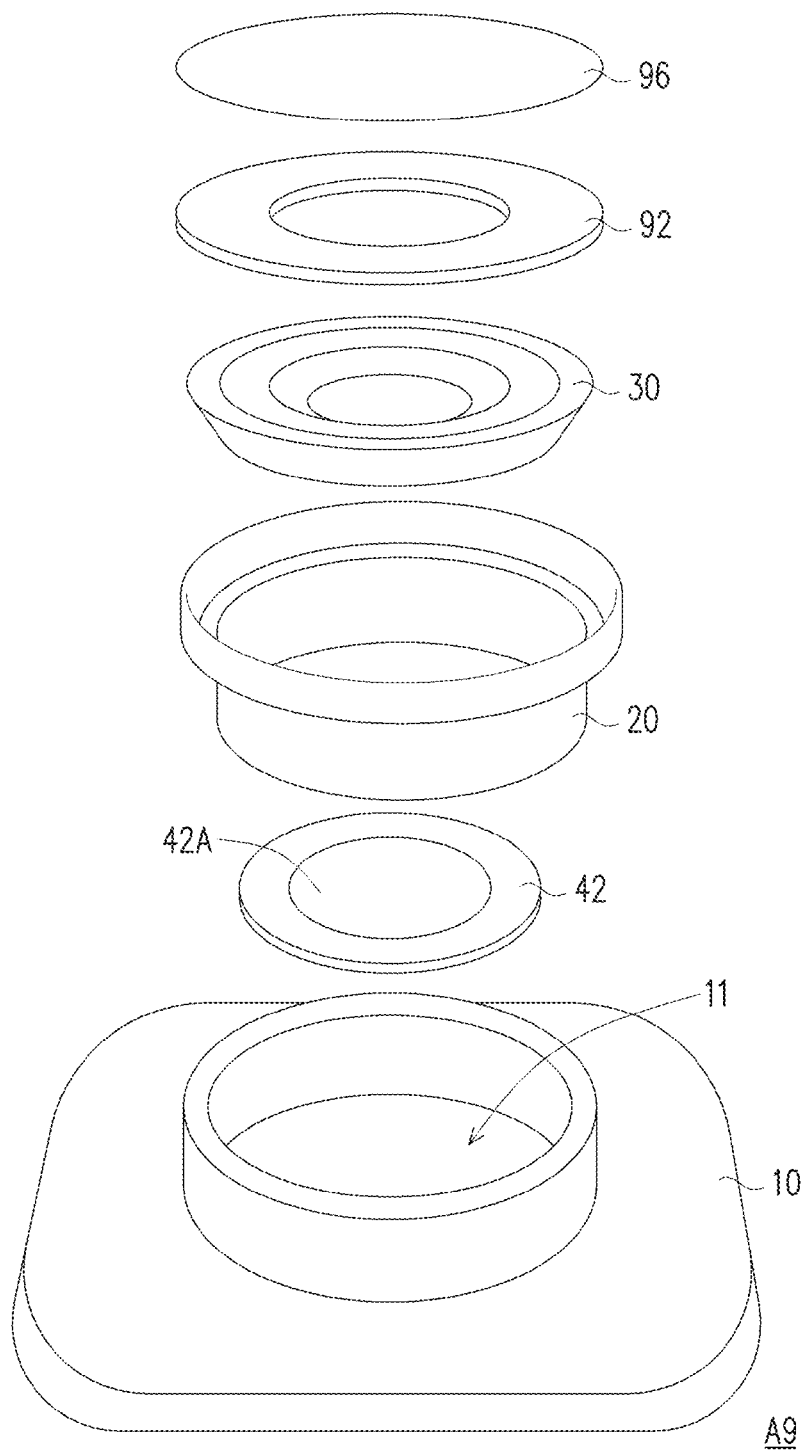

Now referring to FIG. 12, a testing equipment A9 with magnifying function can further include a specimen collection sheet 42 disposed in the specimen holding area 11. The specimen collection sheet 42, for example, has a specimen collection area 42A. The specimen collection area 42A can use adhesion or other methods to collect sperms, subcutaneous tissue/cells, parasite eggs and the like solid test bodies. In some embodiments, the specimen collection sheet 42 can serve as a spacer to maintain a distance between the cover 20 and the specimen holding area 11.

Figure 13:
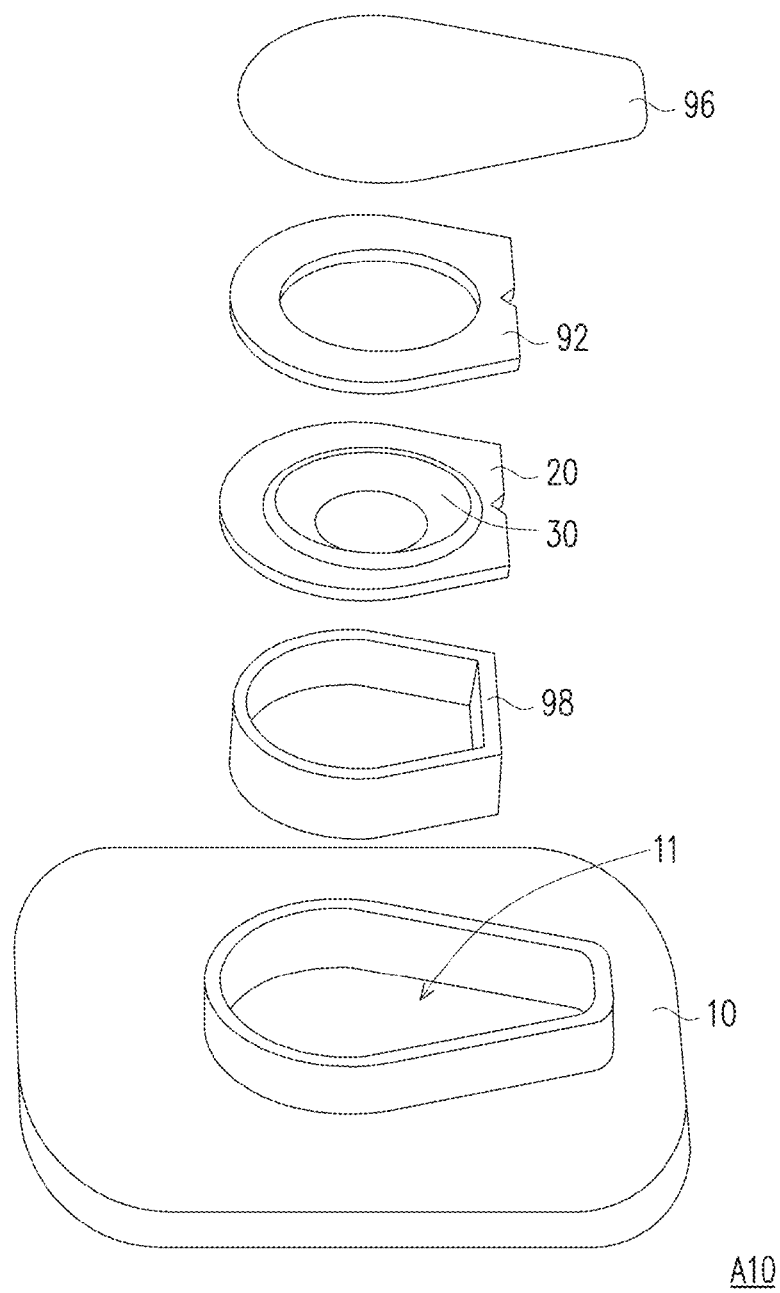

Next, referring to FIG. 13, a testing equipment A10 with magnifying function can include an isolation component 98 disposed at the specimen holding area 11 between the carrier 10 and the cover 20. The isolation component 98 can isolate the magnifying part 30 and the testing fluid in the specimen holding area 11, and prevent the testing fluid from contaminating the magnifying part 30. In some embodiments, the isolation component 98 can serve as a spacer to maintain a distance between the cover 20 and the specimen holding area 11. The isolation component 98 can be integrated with the cover 20 as a single component. Alternatively, the isolation component 98 can be integrated with the carrier 10 as a single component.

Figure 14A:
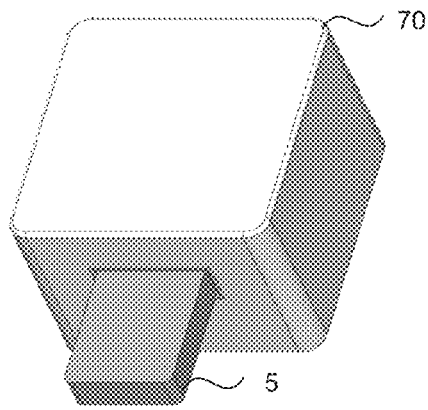
FIG. 14A is a schematic diagram of a test strip inserted into a meter device according to another embodiment of the invention.

FIG. 14A is a schematic diagram of a test strip inserted into a meter device according to another embodiment of the invention. The test strip 5 (also referred to test cartridge) includes a detachable cover 20 and a carrier 10. In other words, a combination of a detachable cover 20 and a carrier 10 (as illustrated in FIG. 1B for example) forms a test strip 5. The test strip 5 in in inserted into a meter device 70 (also referred to as base component) through an insertion port. The insertion port can be, e.g., a lateral or vertical insertion port. The meter device 70 can include, e.g., components for capturing images of specimen collected in the test strip 5.

Figure 14B:
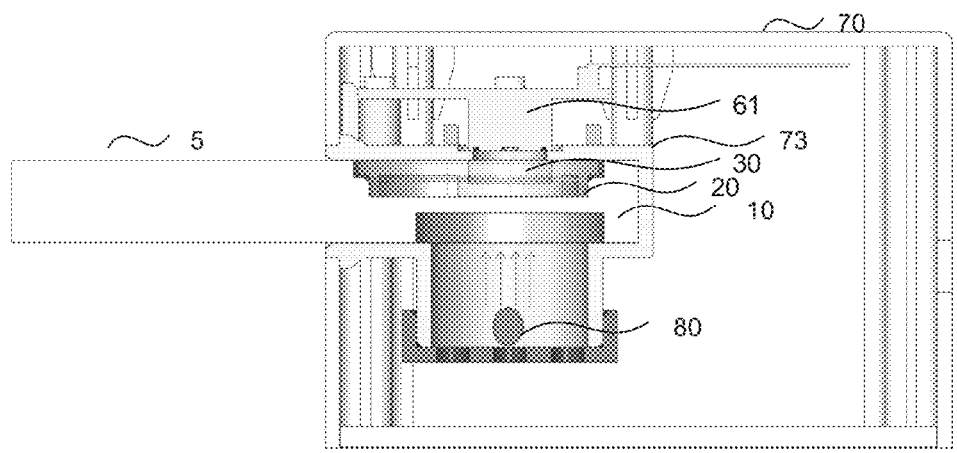
FIG. 14B is a schematic diagram of components of a meter device according to another embodiment of the invention.
Figure 15A:
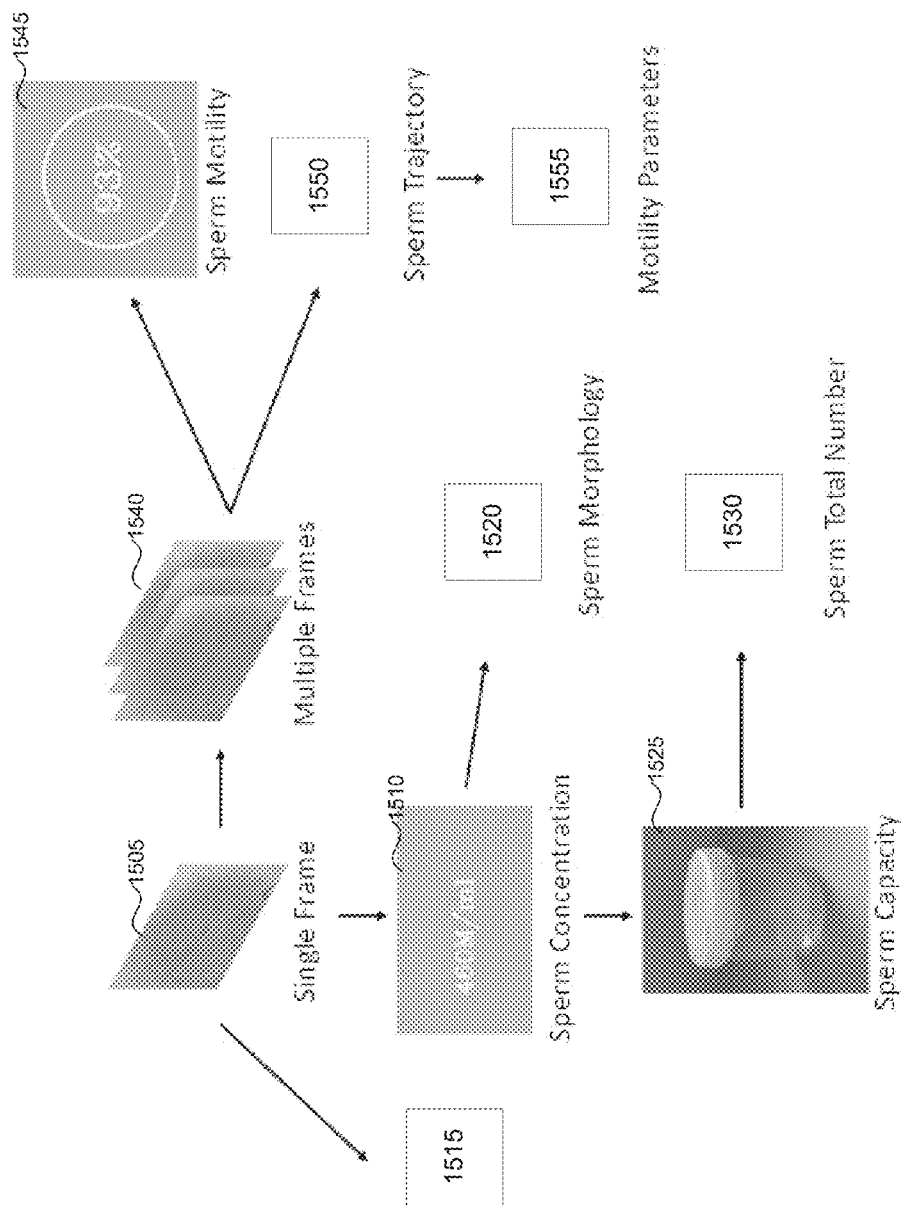
FIG. 15A illustrates a sample process of a semen test by device such as a meter device or an intelligent communications device.
Figure 15B:
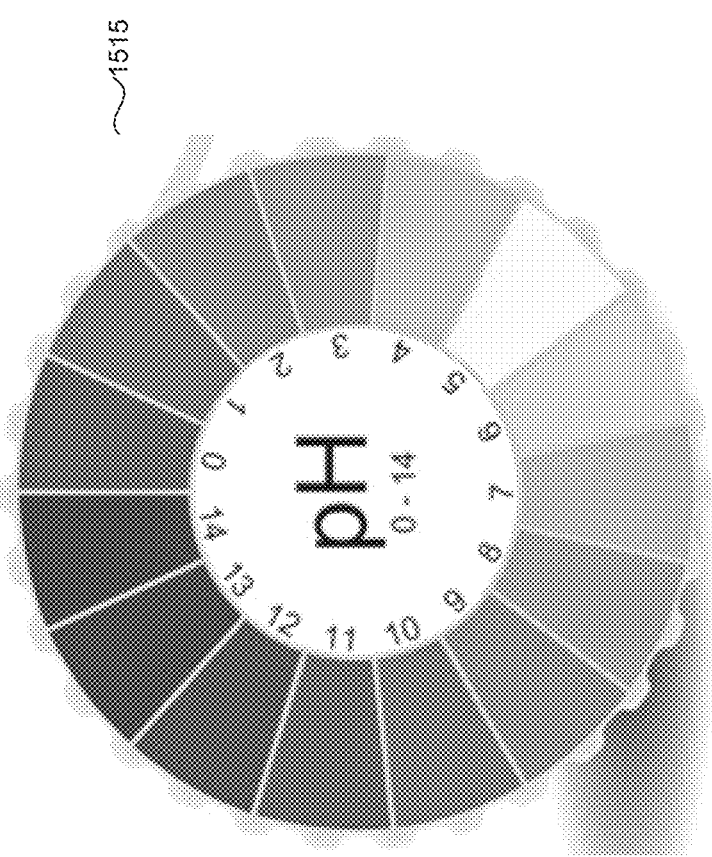
FIG. 15B illustrates a sample step 1515 of the process illustrated in FIG. 15A.
Figure 15C:
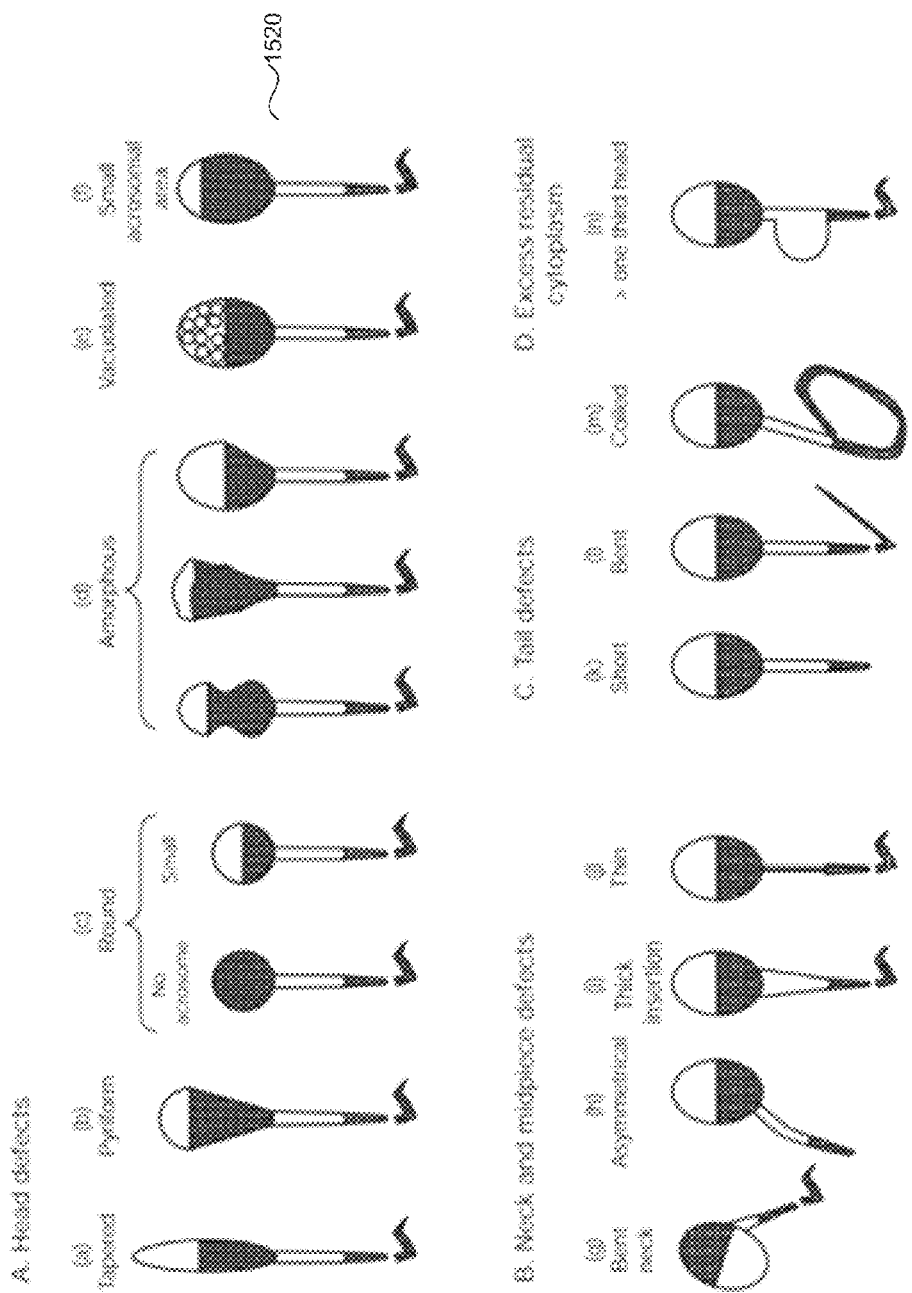
FIG. 15C illustrates a sample step 1520 of the process illustrated in FIG. 15A.
Figure 15D:
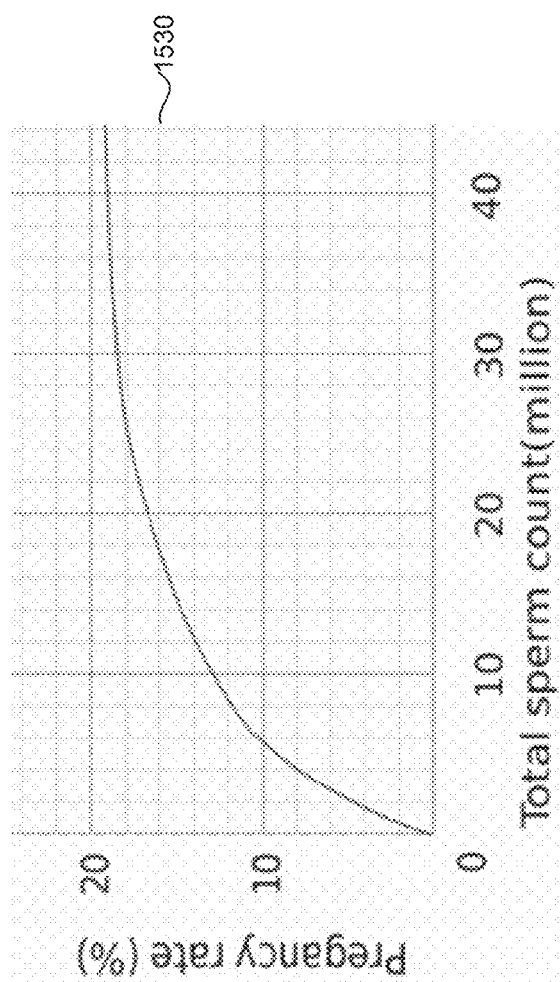
FIG. 15D illustrates a sample step 1530 of the process illustrated in FIG. 15A.
Figure 15E:
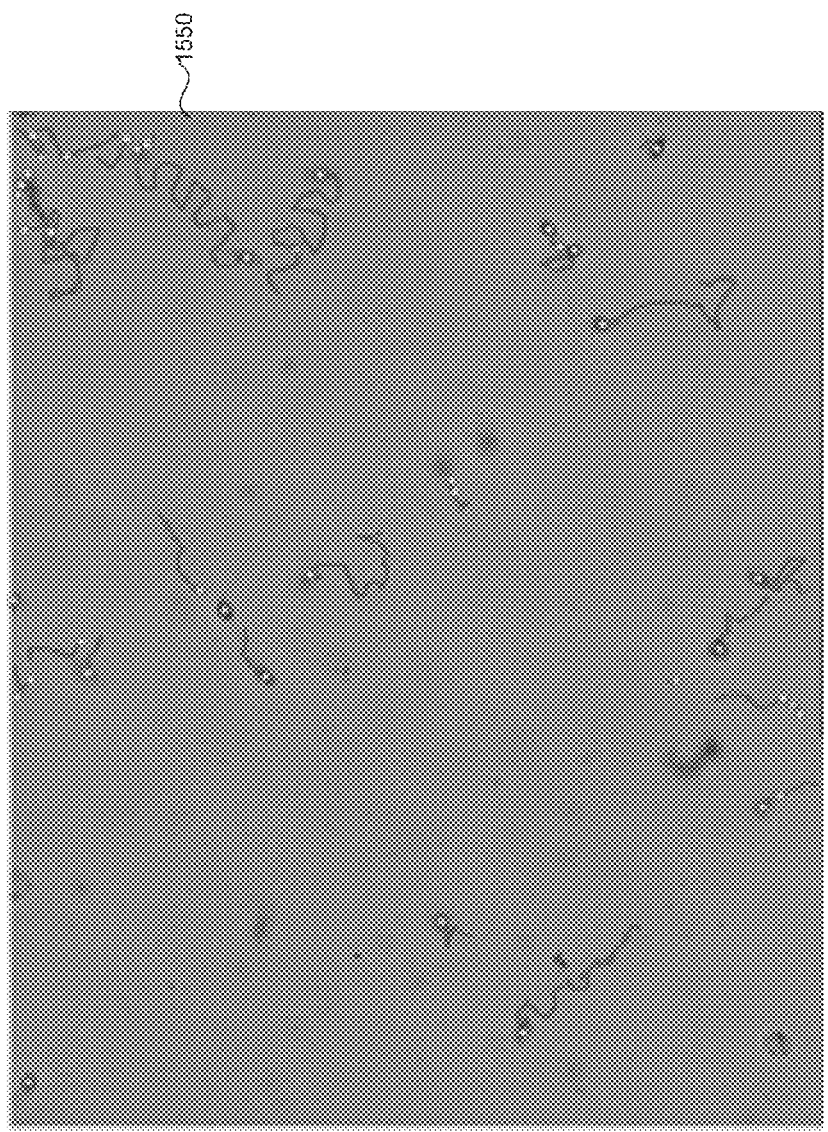
FIG. 15E illustrates a sample step 1550 of the process illustrated in FIG. 15A.
Figure 15F:
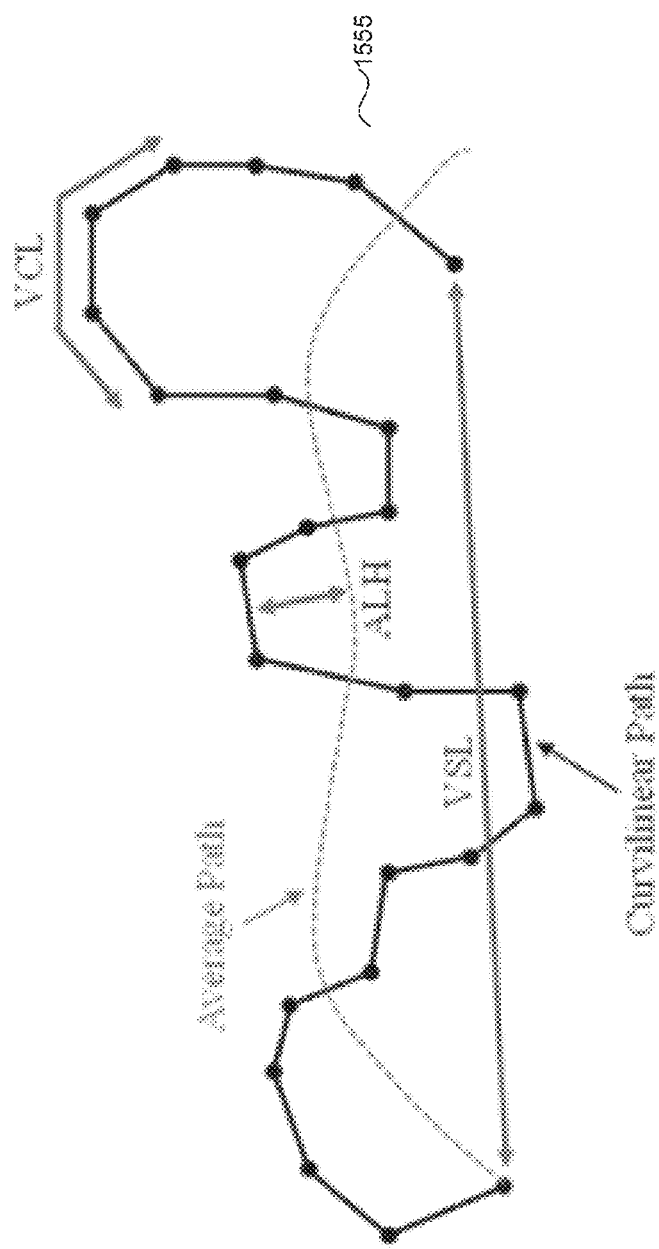
FIG. 15F illustrates a sample step 1555 of the process illustrated in FIG. 15A.

FIG. 14B is a schematic diagram of components of a meter device according to another embodiment of the invention. The meter device 70 includes an insertion port 73 providing an insert position for the strip 5. The strip 5 includes a carrier 10 and a detachable cover 20. The detachable cover includes a magnifying component 30. The meter device 70 includes a camera 61 for capturing images or videos of the specimen holding area of the carrier 10. The camera 61 is aligned with the magnifying component 30. The meter device further includes a light source 80 for provide illumination for the specimen holding area from the bottom. In some embodiments, a light collimator (e.g., a collimating lens or a light reflector; now shown) can be placed on top of the light source 80 for collimating the light beams. An annular diaphragm can be further placed between the light source 80 and the light collimator so that the light beams travelling through the light collimator form a hollow cone of light beams. The carrier 10 can include transparent or translucent materials for light prorogation.

In some embodiments, the meter device 70 can further include a phase plate for shifting phases of light rays emitted from the specimen holding area. When light rays propagate through the specimen, the speed of light rays is increased or decreased. As a result, the light rays propagating through the specimen are out of phase (by about 90 degrees) with the remaining light rays that do not propagate through the specimen. The out-of-phase light rays interfere with each other and enhance the contrast between bright portions and dark portions of the specimen image.

The phase plate can further shift the phases of the light rays propagating through the specimen by about 90 degrees, in order to further enhance the contrast due to the interference of out-of-phase light rays. As a result, the light rays propagating through the specimen are out of phase, by a total of about 180 degrees, with the remaining light rays that do not propagate through the specimen. Such a destructive interference between the light rays enhances the contrast of the specimen image, by darkening the objects in the image and lightening the borders of the objects.

In some alternative embodiments, such a phase plate can be disposed on top of the detachable cover 20 of the strip 5. In other words, the phase plate can be part of the strip 5, instead of part of the meter device 70.

FIG. 15 illustrates a sample process of a semen test by device such as the meter device 70 or the intelligent communications device 60 as illustrated in FIGS. 5 and 14 respectively. At step 1505, the device obtains an image (frame) of the specimen. At step 1510, the device determines the sperm concentration based on the image. By analyzing the color or the grayscale of the pH strip, at step 1515, the device can further determine the pH value of the specimen. For example, the device can include a processor to identify the color of a portion of an image which is captured by camera, corresponding to the pH strip and to determine a biochemical property (e.g., pH level) of a biological specimen contained in the strip. In some other embodiments, the light source of the device can provide illumination with at least one color. For example, the light source can include light emitters with different colors (e.g., red, green and blue) to form light of various colors. The camera of the device can further capture at least one (or more) image of the sample being illuminated with light The processor can compare the colors of a specific region (e.g., pH strip region) of the images to determine a property of the biological specimen or quantification of analyte. In some embodiments, the processor only needs a color of the specific region of one image to determine a property of the biological specimen. For example, the device (e.g., a testing equipment) can include a color calibration module for calibrating the color of the image. The processor then analyzes the calibrated image to determine the property of the biological specimen. Alternatively, the test strip can include a color calibration area that has a known color. The processor conducts a color calibration operation on the image based on the color calibration area, and then analyzes the calibrated image to determine the property of the biological specimen or quantification of analyte. In some embodiments, the reagent in the pH strip (or other types of biochemical test strips) reacts with the biological specimen, before the specific region (e.g., pH strip region) of the images shows specific color(s). In some embodiments, the specific region for color detection does necessarily need a magnification for the images captured by the camera. Thus, at least in some embodiments, there is no magnifying component or supplement above a specific region of the strip for color detection (e.g., pH strip region). For example, some types of biochemical test strips contain photochemical reagents. When a photochemical reagent reacts with a specific analyte in the biological specimen, the reaction causes a color change in the specimen holding area of the ship. The processor can analyze the image of the test strip (captured by the camera) to detect the color change and to quantify the specific analyte in the biological specimen. Furthermore, the device can determine the sperm morphology (1520), sperm capacity (1525) and sperm total number (1530). At step 1540, the device obtains a series of multiple frames of the specimen. At steps 1545, 1550 and 1555, the device can determine the sperm motility parameters based on the sperm trajectory and determine the sperm motility.

Figure 16:
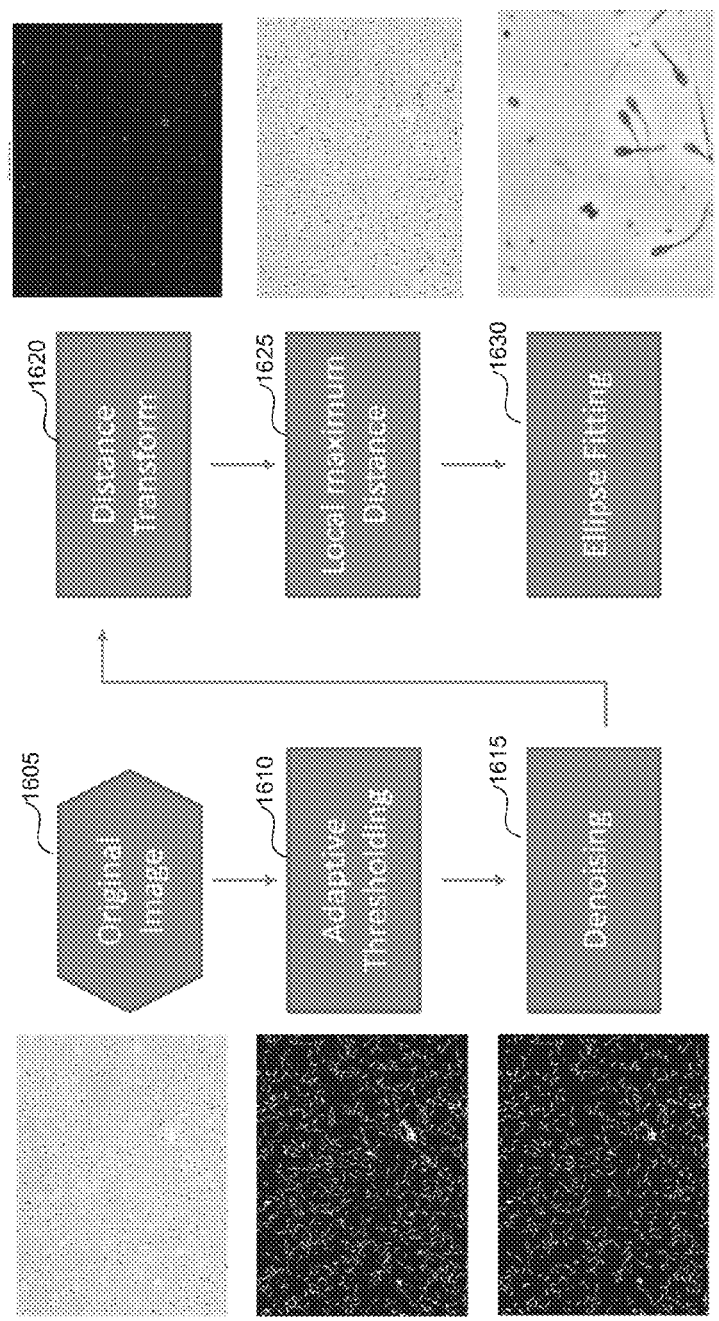
FIG. 16 illustrates a sample process of determining sperm concentration.

FIG. 16 illustrates a sample process of determining sperm concentration. At 1605, a camera of the meter device 70 or the intelligent communications device 60 ("the device"), as illustrated in FIGS. 5 and 14 respectively, captures a magnified image of the sperm specimen. The captured image is an original image for the determining the sperm concentration. The device then converts the digital color image into digital grayscale image, and further divides the digital grayscale image into multiple regions.

At step 1610, the device conduct an adaptive thresholding binarization calculation on each region, based on the mean value and standard deviation of the grayscale values of that region. The goal of the adaptive thresholding binarization calculation is to identify objects that are candidates of sperms as foreground objects, and to identify the rest of the region as background.

Foreground objects in the image after the binarization calculation may still include impurities that are not actually sperms. Those impurities are either smaller than the sperms or larger than the sperms. The method can set an upper boundary value and a lower boundary value for the sizes of the sperms. At step 1615, the device conducts a denoising operation on the image by removing impurities that are larger than the upper boundary value or smaller than the lower boundary value for the sperms. After the denoising operation, the foreground objects in the image represent sperms.

The method counts the number of sperms in the image based on the head portions of the sperms. At steps 1620 and 1625, the device conducts a distance transform operation to calculate a minimum distance between the foreground objects and the background, and also identify locations of local maximum values. Those locations are candidates of sperm head locations.

At step 1630, the device conducts an ellipse fitting operation to each sperm candidate object to reduce false positive candidates that do not have ellipse shapes and therefore are not sperm heads. Then the device counts the total number of remaining positive candidates of sperms, and calculates the concentration of the sperms based on the volume represented by the image. The volume can be, e.g., the area of the captured specimen holding area times the distance between the specimen holding area and the bottom of the cover.

In some embodiments, the device can use multiple images of the specimen and calculate concentration values based on the images respectively. Then the device calculates an average value of the concentration values to minimize the measurement error of the sperm concentration.

Figure 17:
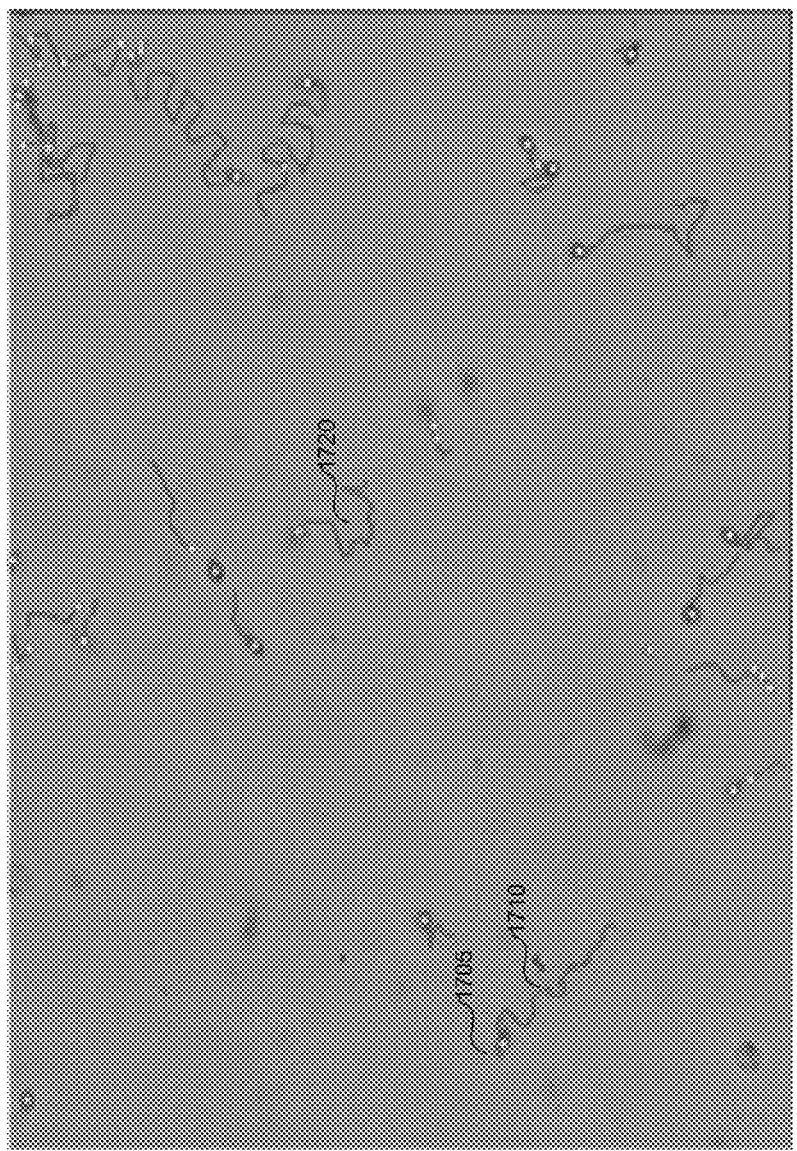
FIG. 17 illustrates sample sperms and sample sperm trajectories.

Using a series of images (e.g., video frames) of the specimen, the device can further determine the trajectories and motility of the sperms. For example, FIG. 17 illustrates sample sperms such as sperm 1705 and sample sperm trajectories such as trajectory 1710 and trajectory 1720.

Figure 18:
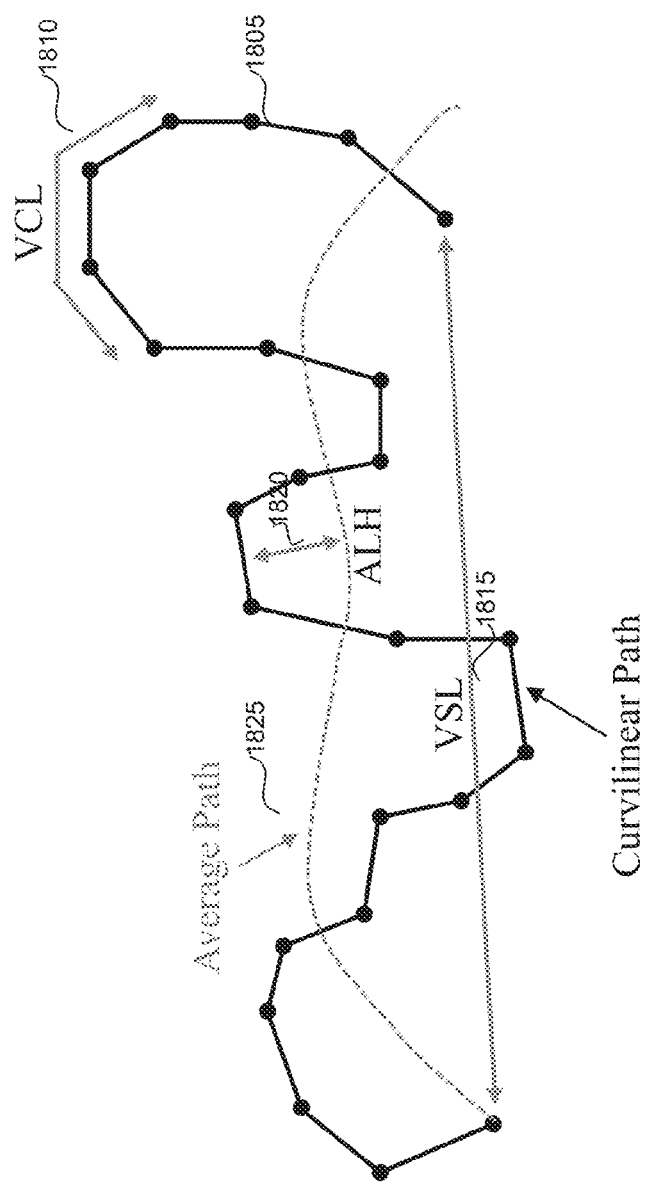
FIG. 18 illustrates a sample process of determining sperm trajectories and motility.

FIG. 18 illustrates a sample process of determining sperm trajectories and motility. A camera of the meter device 70 or the intelligent communications device 60 ("the device"), as illustrated in FIGS. 5 and 14 respectively, captures a series of images (e.g., video frames) of the sperm specimen. The device uses the captured series of images for determining parameters of sperm motility. In order to determine the parameters of sperm motility, the device needs to track the trajectory of each sperm in the series of images.

The device converts the digital color images into digital grayscale images. The device first identifies the head positions of sperms in the first image of the series (e.g., using a method illustrated in FIG. 16). The identified head positions of the sperms in the first image are the initial positions for the sperm trajectories to be tracked. In some embodiments, the device can use a two-dimensional Kalman filter to estimate the trajectory for the movement of the sperms. In some embodiments, the two-dimensional Kalman Filter for tracking sperm $s_j$ with measurement $z_j(k)$ includes steps of:

1: Calculate the predicted state $\hat{x}_{s_j}(k|k-1)$ and error covariance matrix $P_{s_j}(k|k-1)$:

$$\hat{x}_{s_j}(k|k-1)=F(k)\hat{x}_{s_j}(k-1|k-1)$$

$$P_{s_j}(k|k-1)=F(k)P_{s_j}(k-1|k-1)F(k)^T+Q(k-1)$$

2: Using the predicted state $\hat{x}_{s_j}(k|k-1)$, the measurement $z_j(k)$ and error covariance matrix $P_{s_j}(k|k-1)$, calculate the predicted measurement $\hat{z}_{s_j}(k|k-1)$, measurement residual $v_{s_j}(k)$ and residual covariance matrix $S_{s_j}(k)$:

$$\hat{z}_{s_j}(k|k-1)=H(k)\hat{x}_{s_j}(k|k-1)$$

$$v_{s_j}(k)=z_j(k)-\hat{z}_{s_j}(k|k-1)$$

$$S_{s_j}(k)=H(k)P_{s_j}(k|k-1)H(k)^T+N(k)$$

3: if $v_{s_j}(k)^T S_{s_j}(k)^{-1} v_{s_j}(k) < \gamma$ and $\|v_{s_j}(k)\|/T \leq V_{max}$ then calculate the Kalman filter gain $K_{s_j}(k)$, updated state estimate $\hat{x}_{s_j}(k|k)$, and updated error covariance matrix $P_{s_j}(k|k)$:

$$K_{s_j}(k)=P_{s_j}(k|k-1)H^T(k)S_{s_j}(k)^{-1}$$

$$\hat{x}_{s_j}(k|k)=\hat{x}_{s_j}(k|k-1)+K_{s_j}(k)v_{s_j}(k)$$

$$P_{s_j}(k|k)=P_{s_j}(k|k-1)-K_{s_j}(k)H(k)P_{s_j}(k|k-1)$$

(k|k−1) denotes a prediction of image k based on image k−1, $\hat{x}_{s_j}$ is the state of position and velocity of j-th sperm. $P_{s_j}$ is the covariance matrix of the estimation error, Q(k−1) is the process noise covariance matrix, N(k) is the covariance matrix of white position noise vector, γ is the gate threshold and $V_{max}$ is the maximum possible sperm velocity.

When tracking multiple trajectories of multiple sperms, the method can use joint probabilistic data association filter to decide the trajectory paths. The joint probabilistic data association filter determines the feasible joint association events between the detection targets and measurement targets. Feasible joint association events ($A_{js}$) is the relative probability values between the detection sperm s and measurement sperm j. Then the method conducts path allocation decisions based on optimal assignment method. $A_{jt}$ is defined as:

$$A_{js} = \begin{cases} -\ln(\lambda^{-1}f_{s_j}[z_j(k)]), \\ \infty, \end{cases}$$

if measurement sperm j is validated by track s
otherwise

λ is the parameter, $f_{s_j}[z_j(k)]$ is the Gaussian probability density function of the detection sperms.

Based on the series of frames within a time period, the method identifies the trajectory of each sperm, such as the trajectory 1805 as illustrated in FIG. 18. Then the method determines various parameters of the sperm mobility based on the trajectories. The parameters include, e.g., curvilinear velocity (VCL), straight-line velocity (VSL), linearity (LIN) and amplitude of lateral head displacement (ALH). The curvilinear velocity (VCL) 1810 is defined as a summation of movement distances within a unit of time. The straight-line velocity (VSL) 1815 is defined as a straight-line movement distance within a unit of time. The linearity (LIN) is defined as VSL divided by VCL. The amplitude of lateral head displacement (ALH) 1820 is defined as twice the amplitude of the lateral displacement of the sperm head relative to the average path 1825.

In some embodiments, the curvilinear velocity (VCL) 1810 can be used to determine the sperm motility. The method can set a velocity threshold value. Any sperms having VCL higher than or equal to the velocity threshold value are identified as active sperms. The rest of the sperms, which have VCL lower than the velocity threshold value, are identified as non-active sperms. The level of motility is the number of identified active sperms divided by the total number of sperms recognized from the images.

The method can further analyze the sperm morphology. A camera of the meter device 70 or the intelligent communications device 60 ("the device") captures a magnified image of the sperm specimen. The captured image is an original image for the determining the sperm morphology.

The method detects the shapes of the sperm candidates based on segmentation. The method uses the locations of heads of the sperms as the initial points. Using a segmentation algorithm that relates to the shapes, the method divides the images of the sperms into head portions, neck portions and tail portions. For example, the method can divide the sperms using methods such as active contour model.

Based on the each portions, the method calculates parameters for the various portions (such as lengths and widths). A classifier (such as support vector machine, neural network, convolutional neural network or adaboost) can be trained using training data set includes samples that are labeled already. After the training, the parameters of the various portions of the sperms can be fed to the classifier to determine whether the sperm has a proper morphology. In some embodiments, the classifier can be used for other applications such as detecting properties of cells and microbes.

Figure 19:
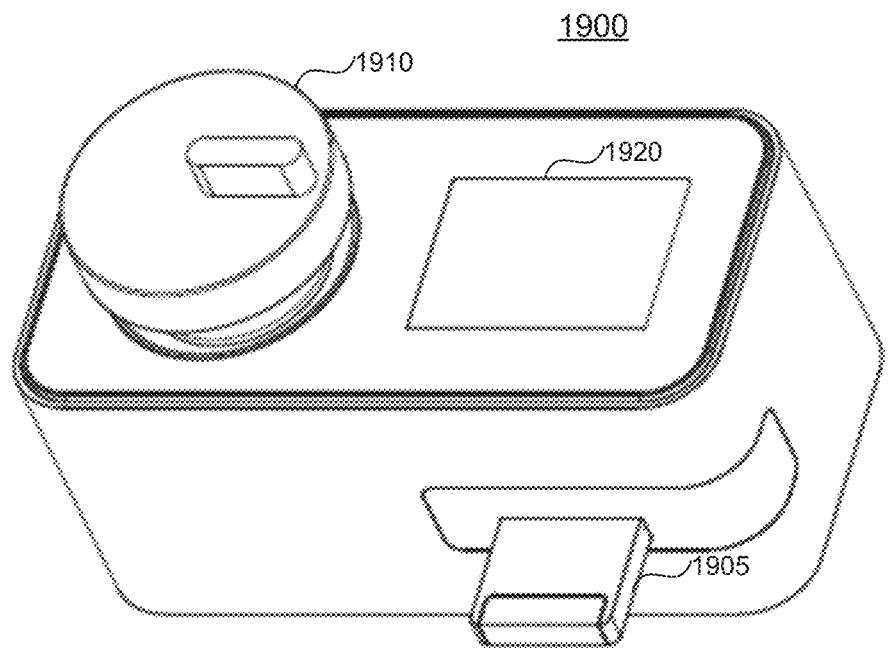
FIG. 19 is a schematic diagram of a testing equipment including a collection bottle.

FIG. 19 is a schematic diagram of a testing equipment including a collection bottle according to at least one embodiment of the invention. A test strip device 1905 can be inserted into the testing equipment 1900 through an insertion port. The test strip device 1905 can include a collection bottle 1910 for collecting the specimen (e.g., sperm specimen) or include a slot for accommodating the collection bottle. The testing equipment 1900 can include a sensor (not shown) to detect whether the collection bottle 1910 is inserted into the testing equipment 1900.

The testing equipment 1900 can have a timer mechanism for determining a time period during which the collection bottle 1910 is being inserted into the testing equipment 1900. Once the collection bottle 1910 containing the specimen is inserted, the testing equipment 1900 can wait for a pre-determined time period (e.g., 30 minutes) for liquefaction of the specimen before prompting a user to transfer the specimen from the collection bottle 1910 to the test strip device 1905. In some embodiments, the testing equipment 1900 can include a camera or a sensor to determine whether the specimen already liquefies.

Furthermore, the testing equipment can include a moving mechanism to apply a mechanical force to the collection bottle 1910 in order to mix specimen in the collection bottle 1910. For example, the moving mechanism can, e.g., shake, vibrate, or rotate the collection bottle 1910. In some other embodiments, the testing equipment can include a rod to be inserted into the collection bottle 1910 and to stir the specimen in the collection bottle 1910.

The testing equipment 1900 optionally can include a screen 1920 for display information. For example, the screen 1920 can show instructions or hints on how to operate the testing equipment 1900. The screen 1920 can also show test results after the testing equipment 1900 conducts the test. Additionally or alternatively, the testing equipment 1900 may include a known communication module so that it may communication (e.g., the analysis results, and/or the images taken by the camera modules) with a user's computing device (e.g., a smart phone with a mobile software application, or a traditional personal computer such as a laptop). The test equipment 1900 is operable to receive an instruction from a user (e.g., from screen 1920 and/or from the aforementioned communication module), and to perform a select number of the automated analytic processes based on the instruction. The testing equipment 1900 can also display results and/or images of the specimen, either on the screen 1920, or to the user's computer (e.g., via aforementioned communication module), or both.

Similar to the testing equipment illustrated in FIGS. 14A and 14B, the testing equipment 1900 can include a camera (not shown) for capturing images or videos of the test strip device 1905. The testing equipment 1900 can further include a processor (not shown) for processing the images or videos for determining test results (e.g., through the process illustrated in FIG. 16).

In some embodiments, for example, the magnifying component 2110 is a magnifying lens. The magnifying power of the magnifying component 2110 can be represented by either angular magnification ratio or linear magnification ratio. An angular magnification ratio is a ratio between an angular size of an object as seen through an optical system and an angular size of the object as seen directly at a closest distance of distinct vision (i.e., 250 mm from a human eye). A linear magnification ratio is a ratio between a size of an image of an object being projected on an image sensor and a size of the actual object.

For example, the magnifying lens can have a focal length of 6 mm, a thickness of 1 mm and a diameter of 2 mm. Assuming 250 mm is the near point distance of a human eye (i.e., the closest distance at which a human eye can focus), the angular magnification ratio is 250 mm/6 mm=41.7×. The distance between the magnifying component 2110 and the specimen holding area 2115 can be, e.g., 9 mm. As a result, a linear magnification ratio can approximate 2. In other words, a size of an image of an object on the image sensor caused by the magnifying component is 2 times a size of the actual object below the magnifying component.

In some embodiments, the magnifying component has a focal length of 0.1-8.5 mm. In some embodiments, the linear magnification ratio of the magnifying component is at least 1. In some embodiments, the linear magnification ratio of the magnifying component is from 0.5 to 10.0.

In some embodiments, a supplemental lens 2135 is placed below the camera module 2130 for further magnifying the image and decreasing the distance between the magnifying component 2110 and the specimen holding area 2115. The effective linear magnification ratio of the whole optical system can be, e.g., 3. In other words, the image of the object captured by the camera module 2130 is has a size that is 3 times size of the actually object in the specimen holding area 2115. In some embodiments, the effective linear magnification ratio of the whole optical system of the testing equipment is from 1.0 to 100.0, preferably from 1.0 to 48.0.

In some embodiments, the image sensor of the camera module has a pixel size of 1.4 µm. Typically a captured image of an object needs to take at least 1 pixel in order to properly analyze the shape of the object. Thus the size of the captured image of the object needs to be at least 1.4 µm. If the linear magnification ratio of the testing equipment is 3, the testing equipment can properly analyse the shape of objects having a size of at least 0.47 µm.

In some embodiments, the image sensor of the camera module has a pixel size of 1.67 µm. Then the size of the captured image of the object needs to be at least 1.67 µm in order to properly analyze the shape of the object. If the linear magnification ratio of the testing equipment is 3, the testing equipment can properly analyse the shape of objects having a size of at least 0.56 µm.

In some embodiments, for example, the length of the whole optical system can be, e.g., 24 mm. The distance between the bottom of the magnifying component and the top of the specimen holding area 2115 can be, e.g., 1 mm. In some embodiments, length of the whole optical system of the testing equipment is from 2 mm to 100 mm, preferably from 5 mm to 35 mm.

Figure 20:
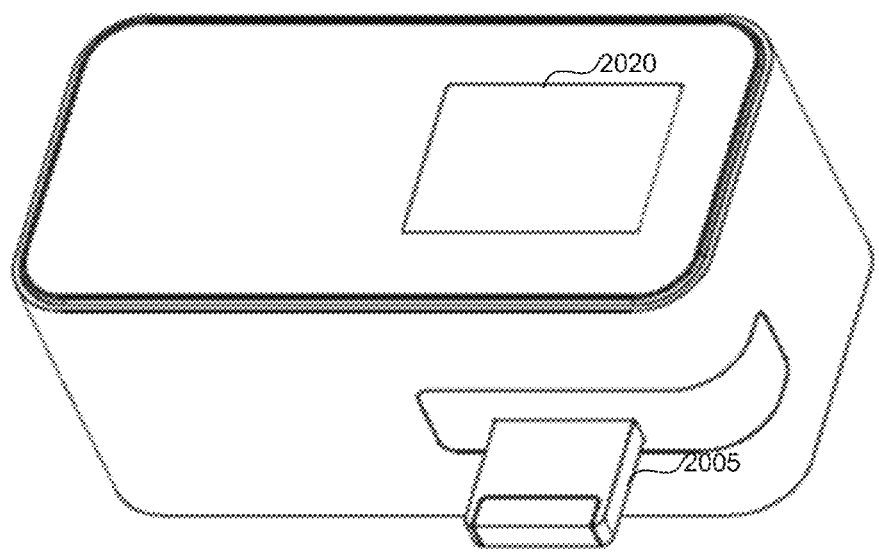
FIG. 20 is a schematic diagram of a testing equipment does not include a collection bottle.

FIG. 20 is a schematic diagram of a testing equipment does not include a collection bottle, according to at least one embodiment of the invention. Unlike the testing equipment 1900, the testing equipment 2000 does not include a collection bottle or a slot for inserting a collection bottle. The specimen is directly applied to the test strip device 2005, by a user or an operator, without being collected in a collection bottle.

Figure 21A:
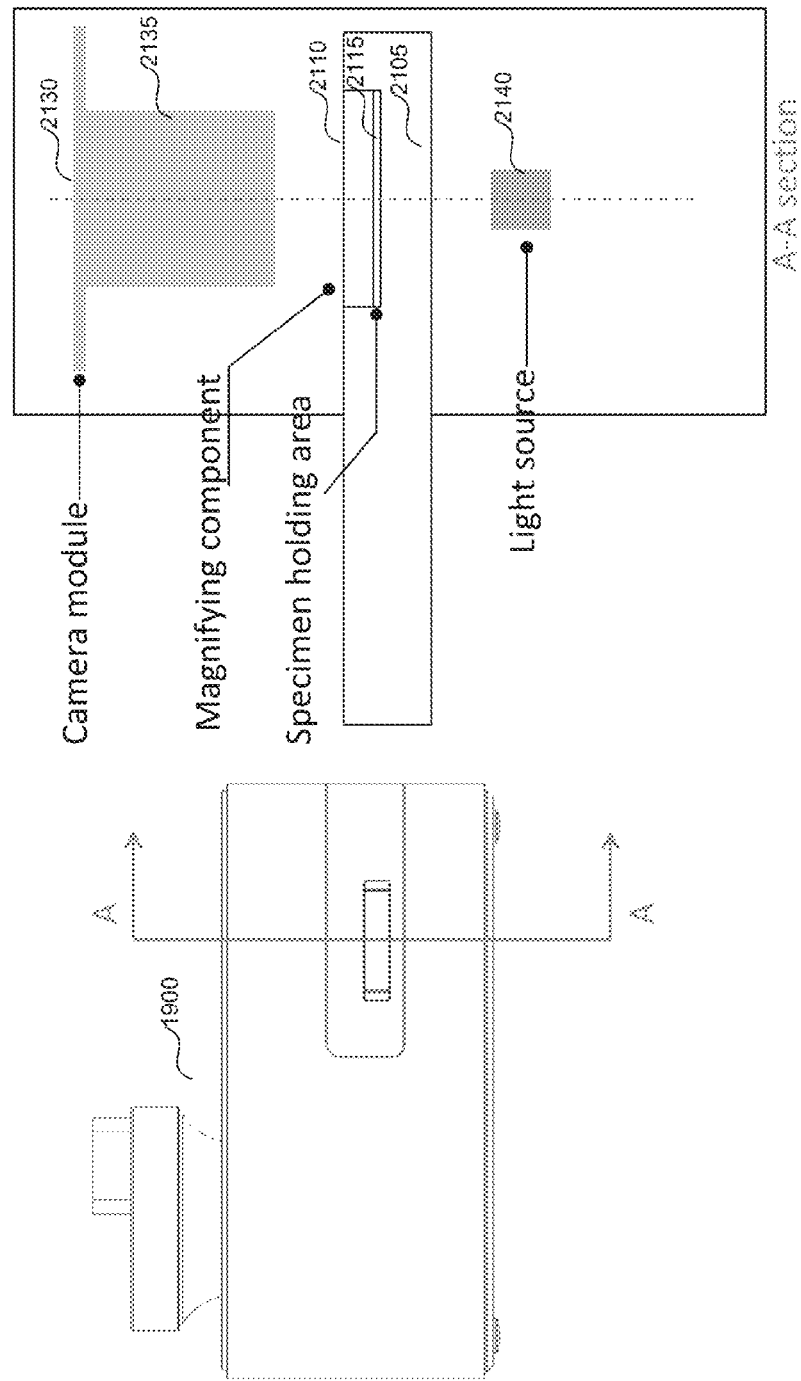
FIGS. 21A and 21B are cross-sectional views of various embodiments of a testing equipment.

FIG. 21A is a cross-sectional view of an embodiment of the testing equipment 1900. The A-A section of the testing equipment 1900 shows a camera module 2130 on top of the test strip device 2105 for capturing images or videos of the specimen holding area 2115 of the test strip device 2105. The test strip device 2105 includes a magnifying component 2110 on top of the specimen holding area 2115. A light source 2140 below the test strip device 2105 provides illumination for the specimen holding area 2115. In some other embodiments, light source can be placed on top of the test strip device or laterally at a side of the test strip device. There can be multiple light sources or an array of light sources for providing illumination on the test strip device. In some embodiments, different combinations of light sources can be switched, adjusted, or selected depending on the analyte types, such that the analyte is illuminated by light with a proper color.

In some embodiments, the test strip device 2105 can include a test strip in or near the specimen holding area 2115. For example, the test strip can be a pH test strip, an HCG (human chorionic gonadotropin) test strip, an LH (luteinizing hormone) test strip or a fructose test strip. When the analyte of specimen in the specimen holding area interacts with the chemical or biochemical agents in the test strip, some optical properties (e.g., color or light intensity) of the test strip can change. The camera module 2130 can capture the color or intensity of the test strip to determine a test result, such as a pH level, an HCG level, an LH level or fructose level. In some embodiments, the magnifying component 2110 above the test strip can be replaced with a transparent or translucent cover. Therefore, the testing equipment can simultaneously conduct a qualification of the analyte in the specimen and conduct a further analysis of the specimen through one or more magnified images of specimen.

Figure 21B:
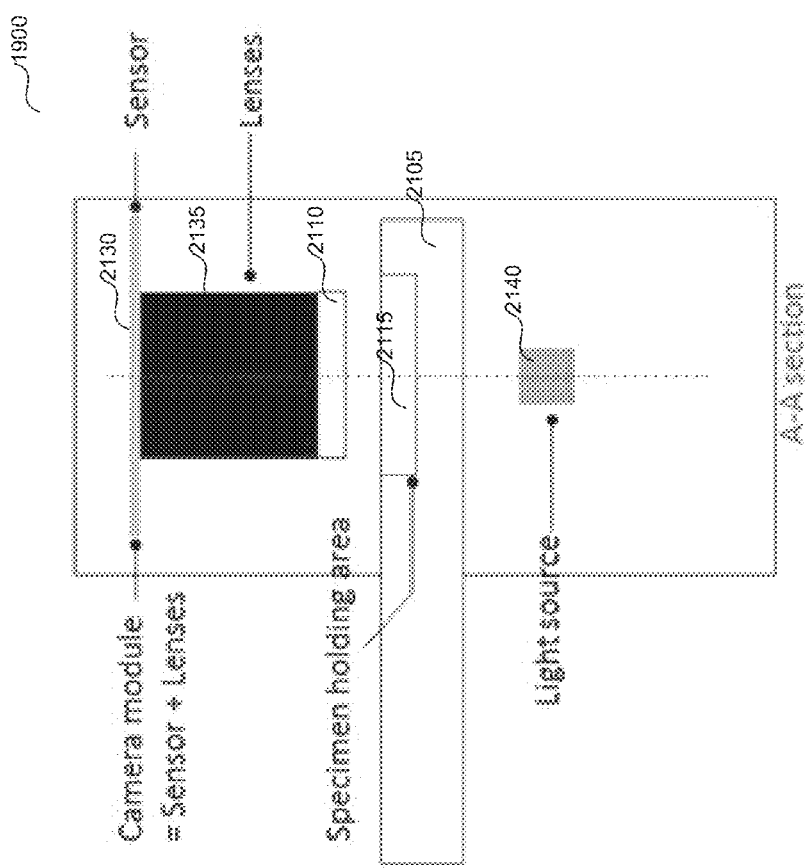

FIG. 21B is a cross-sectional view of another embodiment of the testing equipment 1900. The A-A section of the testing equipment 1900 shows a camera module 2130, which includes a sensor and one or more lenses 2135 (also referred to as supplemental lenses or optical lens module), on top of the test strip device 2105 for capturing images or videos of the specimen holding area 2115 of the test strip device 2105. A light source 2140 below the test strip device 2105 (or disposed at other places) provides illumination for the specimen holding area 2115. A magnifying component 2110 can be attached to the bottom of the lenses 2135, instead of being on top of the specimen holding area 2115 as illustrated in FIG. 21A. In some embodiments, the element 2110 can be a flat light-transmissive cover having no magnification power, if the lenses 2135 provide enough magnification power. In some other embodiments, the testing equipment 1900 does not include the magnifying component 2110, if the lenses 2135 provide enough magnification power (e.g., if the linear magnification ratio of the lenses 2135 is at least 1.0).

Figure 22:
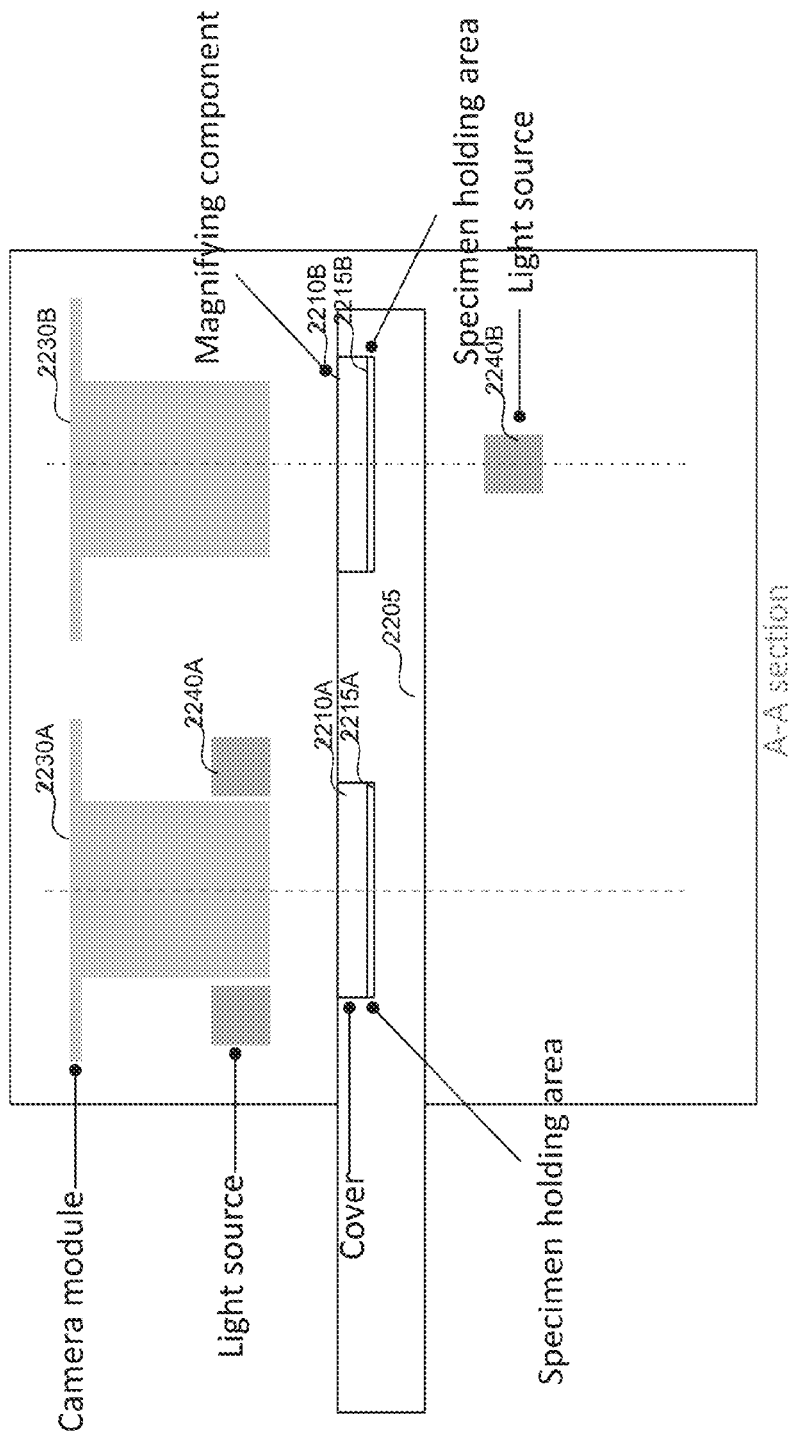
FIG. 22 is a schematic diagram of a testing equipment for a test strip device having two specimen holding area.
Figure 29:
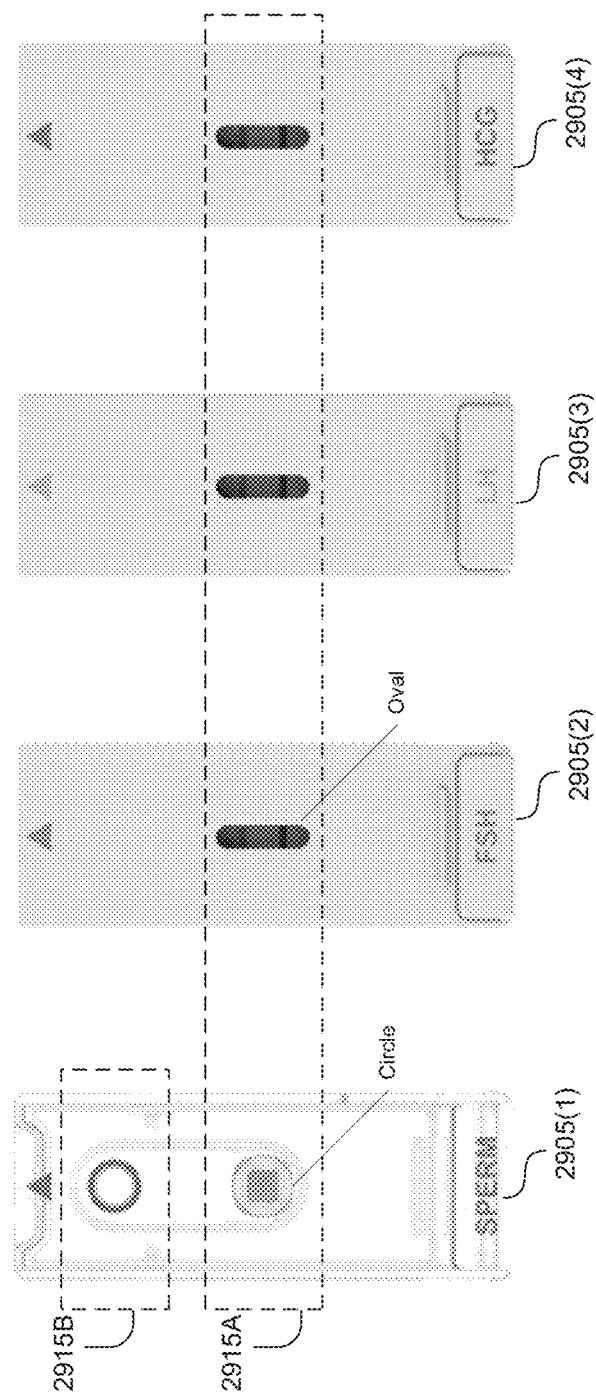
FIG. 29 shows examples of carriers that may be suitable for a test equipment with a multi-camera configuration, such as the test equipment shown in FIG. 22.

FIG. 22 is a schematic diagram of a testing equipment for a test strip device having two specimen holding areas. FIG. 29 shows examples of carriers that may be suitable for a test equipment with a multi-camera configuration, such as the test equipment shown in FIG. 22. With simultaneous reference to FIGS. 19 and 20, the test equipment shown in FIG. 22 can be another variant of the testing equipment 1900 (i.e., with a collection bottle) or the testing equipment 2000 (i.e., without the collection bottle). As shown in FIG. 22, a receiving mechanism is included in the test equipment to receive one or more carriers (e.g., a test strip device, such as test strip device 2205, or a collection bottle such as bottle 1910), which can be inserted through the opening(s) on the casing of the test equipment.

In some embodiments, a single carrier can include a first holding area and a second holding area, such as shown by the test strip device 2205 in FIG. 22. As shown in FIG. 22, at least two camera modules can be included in the test equipment. The two camera modules includes a first camera module 2230A and a second camera module 2230B, arranged to capture images and/or videos of the first holding area 2215A and the second holding area 2215B, respectively. More specifically, the test strip device 2205 can include a specimen holding area 2215A and another specimen holding area 2215B. In some examples, a transparent or translucent cover 2210A is placed on top of the specimen holding area 2215A. The light source 2240A can be controllable and can provide illumination on the specimen holding area 2215A. The camera module 2230A is positioned to capture images or videos of the specimen holding area 2215A. As an optional implementation, a magnifying component 2210B can be placed on top of the specimen holding area 2215B. Further, in some embodiments, the light source 2240B is operable to provide illumination on the specimen holding area 2215B. The camera module 2230B is positioned to capture images or videos of the specimen holding area 2215B. The first and second holding areas may directly carry the biological specimen or have been exposed to the biological specimen. Similar to the structures introduced with respect to FIG. 14B, in some embodiments, the test equipment can include a light collimator for collimating light beams emitted from the light source to at least one of the holding areas. In some embodiments, an annular diaphragm can be further included between the light source and the light collimator for forming a hollow cone of light beams that travels through the light collimator and then reaches the specimen holding area. In some additional embodiments, a phase plate can be included between the specimen holding area and at least one of the camera modules for phase-shifting light rays reflected from the specimen holding area.

As an alternative to a single carrier having multiple holding areas, multiple carriers can be inserted into the test equipment through their respective openings, ports, or slots. For example, two separate test strips devices can include the specimen holding areas 2215A and 2215B respectively. Depending on the need of the test, the location of the specimen holding areas 2215A and 2215B in the test strips can be designed to be aligned with the camera modules 2230A and 2230B. In some embodiments, the two test strip devices are inserted into the testing equipment through two separate insertion ports.

Among other benefits, the convenience and easiness of testing are two prominent benefits that the test equipment disclosed here can provide. According to the present embodiments, a user of the disclosed test equipment need not possess any professional knowledge on how to perform various types of analysis on the biological specimen before the user can utilize the test equipment to produce a result. Accordingly, the test equipment can include a processor for performing automated analytic processes on the specimen and determine an outcome with regard to the specimen. The processor can be carried by a main circuit board (i.e., a known component, not shown for simplicity). Further, the test equipment is preferably small and not as bulky as traditional test equipment commonly seen in the laboratories. Accordingly, in some embodiments, such as those shown in FIGS. 19 and 20, the receiving mechanism for the carrier, the camera modules, and the main circuit board can all be enclosed within the casing of the test equipment. The test equipment may have a small form factor, such as smaller than 30 cm×30 cm×30 cm, that is, 27,000 cm$^3$. In some embodiments, the test equipment can further include a battery compartment enclosed within the casing, such that a battery can be installed in the battery compartment to power the test equipment.

In some embodiments, the processor included in the test equipment can perform different analysis on different holding areas, and can derive the result based on a combination of results from the analyses performed on the different areas. In other words, the processor can be configured to perform a first analytic process on the captured images of the first holding area, to perform a second analytic process different from the first analytic process on the captured images of the second holding area, and to determine an outcome with regard to the biological specimen based on results from both the first and the second analytic processes. As used herein, the term "analytic process" means a process that can evaluate one or more pieces of information collected from a number of sources (e.g., the images of the holding areas), and produce a result, a conclusion, an outcome, an estimate, or the like, regarding the source.

According to some examples, the testing equipment can use a combination of the camera module 2230A, light source 2240A and cover 2210A to quantify an analyte or to determine a property of the specimen (e.g., pH level, LH level, HCG level, or fructose level). Additionally, the testing equipment can further use a combination of the camera module 2230B, light source 2240B and magnifying component 2210B to analyse a magnified image of the specimen to determine properties of the specimen (e.g., sperm quantity, sperm motility, sperm morphology, etc.). Depending on the requirements of various types of biochemical tests, different combinations or configurations of light source(s) can be used to illuminate the biochemical specimen. The multi-camera configuration is particularly advantageous because different analytic processes can be performed through different camera modules without the need for the user to change the carrier (e.g., test strip device), thereby expediting the outcome generation and reducing the complexity of necessary human operation. The light sources 2240A and 2240B are enclosed inside the casing and arranged to illuminate the biological specimen for at least one of the camera modules. According to one or more embodiments, the processor is configured to control the light source based on which analytic process that the processor is currently configured to perform.

Moreover, in some embodiments, the processor can perform different analytic processes based on a visual cue on the carrier. For example, some embodiments can perform image recognition and processing on the images of the holding areas, and can perform different analytic processes according to a visual cue from the results of the image recognition. Example carriers 2905(1)-2905(4) are shown in FIG. 29, where carrier 2905(1) is for fertility testing with regard to reproductive cells for a male subject (e.g., via his sperm), and carriers 2905(2), 2905(3) and 2905(4) are for fertility testing with regard to reproductive cells for a female subject (e.g., via her urine). As shown, the carriers 2905(1)-2905(4) all have a first holding area 2915A that corresponds to the location of the first camera module 2230A, but only the carrier 2905(1) includes a second holding area 2915B. In some examples, the visual cue on the carrier can be a shape of a particular holding area (e.g., the holding area 2215A). For the discussion herein, a shape of a holding area means the general periphery (or an outer perimeter) of the holding area. For example, the shape may be a circle, an oval, a triangle, a rectangle, or any suitable shape that is identifiable by a processor utilizing known image processing techniques on images of the holding area as captured by a respective camera module (e.g., camera module 2230A). Additional example of the visual cue may include a graphic pattern, a visual indicia, a one-dimensional barcode, a multi-dimensional pattern code (e.g., QR code), and so forth.

With simultaneous reference to FIGS. 22 and 29, in some embodiments, when the processor identifies (e.g., via the first camera module 2230A) that the first holding area (e.g., area 2215A, or area 2915A of carrier 2905(1)) be in a first shape (e.g., a circle), the processor is configured to perform a certain analytic process (e.g., fertility of a male subject, such as from various properties of his sperm sample), and when the first holding area (area 2215A, or area 2915A of carrier 2905(2)) is in a second shape (e.g., an oval), the processor is to perform a different analytic process (e.g., analysis of fertility of a female subject, such as from the hormone level of her urine sample). In this way, not only is the test equipment not limited to perform only one type of test (e.g., fertility of sperm), but it can also switch the analytic processes accordingly based on the carrier (e.g., test trip device) inserted into the machine.

More specifically, according to some implementations, when the shape represents that the biological specimen includes sperm from a male subject, then the process can determine one or more properties of the sperm, such as those introduced herein. The determination of the one or more properties of the sperm may be performed, in some examples, by using the second camera module 2230B. For some specific examples, the properties can be determined may include: a concentration of the sperm, a motility of the sperm, and/or a morphology of the sperm. According to some embodiments, the processor is configured to (1) determine a concentration of the sperm and/or a morphology of the sperm based on a single image from the captured images, and (2) determine a motility of the sperm based on two or more images from the captured images.

Figure 30:
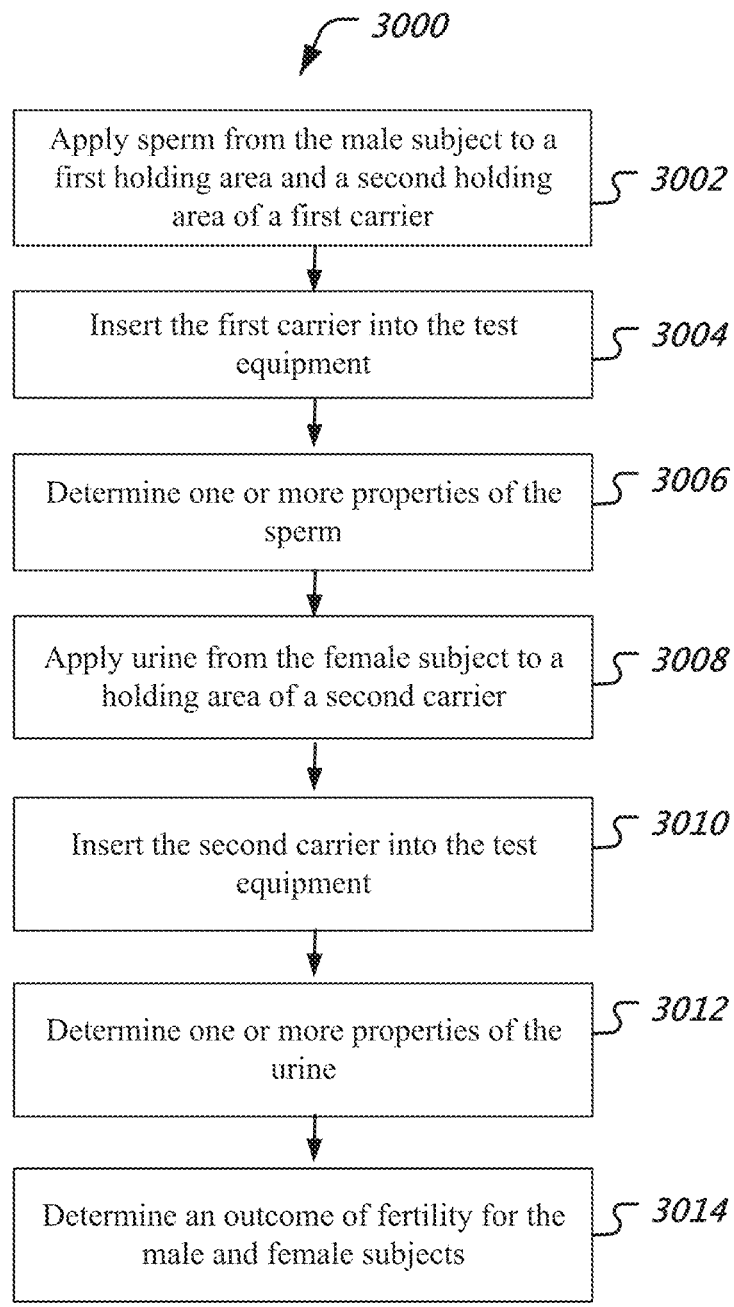
FIG. 30 is a flow chart of a process for utilizing a test equipment disclosed here to analyze fertility for both a male subject and a female subject.

With the above in mind, FIG. 30 is a flow chart of an example process 3000 for utilizing a test equipment disclosed here (e.g., in FIG. 22) to analyze fertility for both a male subject and a female subject. With continued reference to FIG. 29, the process 3000 is explained below. Note that the following example applies the specimen from male first then female, but the reverse order (i.e., female and then male) can be performed with no effect on the accuracy of the result.

First, in step 3002, the user can apply a biological specimen (e.g., sperm) from the male subject to a first holding area (e.g., area 2915A) and a second holding area (area 2915B) of a first carrier (e.g., carrier 2905(1)). Next, in step 3004, the user is to insert the first carrier into the test equipment (e.g., such as the one shown in FIG. 22), and because the shape of the first holding area 2915A of carrier 2905(1) is circle, the test equipment can automatically acquire the knowledge that the current specimen contains sperm from a male and selects analytic processes accordingly. Then, in step 3006, the user can use the test equipment to determine one or more properties of the sperm. For example, as discussed here, the processor in the test equipment can utilize the first camera module 2230A to take images of the first holding area 2915A of the carrier 2095(1), which can include a test strip that shows different color in response to different acidity, and recognize the color of the test strip to determine the acidity of the sperm. Additionally, in step 3006, the processor in the test equipment can utilize the second camera module 2230B to determine one or more properties of the sperm selected from the group consisting of: concentration of the sperm, motility of the sperm, and morphology of the sperm;

Next, in step 3008, the user can apply urine from the female subject to a holding area 2915A of a second carrier (e.g., carrier 2905(2)). In step 3010, the user inserts the second carrier into the test equipment, and because the shape of the first holding area 2915A of carrier 2905(2) is oval, the test equipment can automatically acquire the knowledge that the current specimen contains urine from a female and selects analytic processes accordingly. In step 3012, the test equipment determines one or more properties of the urine, e.g., by utilizing the second camera module 2230B. For example, the test strip may be suitable for enabling the test equipment to determine a concentration level of one or more types of female hormones (e.g., FSH, LH, or HCG). Lastly, in step 3014, the user utilize the test equipment to automatically analyze the results of the male and the female biological specimen and determine an outcome with regard to the subjects' fertility.

In some specific examples, the first camera module 2230A may have a lower camera resolution than the second camera module 2230B, and therefore the two cameras are utilized by the processor to perform different analytic processes. Additionally, the first camera module 2230A may have a lower magnifying ratio than the second camera module 2230B. Some examples of the first camera module 2230A may have no magnifying function at all, while the second camera module 2230A may have a fixed magnifying ratio. In addition or as an alternative to the second camera module 2230B itself having a higher magnifying ratio, the cover 2210B for the second holding area 2215B can include a magnifying component, such as illustrated in FIG. 22. In some implementations, the magnifying ratio of the camera modules may be adjustable (e.g., as controlled by the processor). Some examples of the test equipment provide that the first camera module 2230A has a camera resolution of 2 megapixels or above, and that the second camera module 2230B has a camera resolution of 13 megapixels or above. In some examples, the second camera module 2230B may include a linear magnifying ratio of at least 4.8 times or above.

In some of these examples, the processor is further to determine at least one additional property of the sperm by using the first camera module 2230A. This additional property may include an acidity of the sperm. For example, the carrier can include a pH indicator in the first holding area 2215A to represent the acidity of the sperm with colors, through which the processor can recognize for identifying the acidity. Similarly, some examples provide that the processor can determine a biochemical property of the biological specimen based on a color of a region in the one or more images of the first or second holding area.

Continuing with the above test equipment examples with multi-camera configurations in FIG. 22 and the carrier examples in FIG. 29, in some implementations, when the processor identifies the first holding area (e.g., area 2215A, or area 2915A of carrier 2905(2)) being in a second shape, such as an oval, which may indicate that the biological specimen includes urine from a female subject, the processor is configured to determine one or more properties of the urine. The properties can be determined can include: an LH level, an FSH level, and/or an HCG level. Like acidity, the determination of the one or more properties of the urine may be performed by using the first camera module. Similarly, the carrier can include an LH indicator (e.g., as shown in carrier 2905(3)), an FSH indicator (e.g., as shown in carrier 2905(2)), and/or an HCG indicator (e.g., as shown in carrier 2905(4)) in the first holding area (e.g., area 2915A of respective carriers).

Furthermore, in some embodiments, the processor can utilize at least one of the two camera modules (e.g., the first camera module 2230A), or another sensor (e.g., light sensor 2690, introduced below with respect to FIG. 26), to determine a readiness or a validity of the biological specimen before performing the analytic processes. In some implementations, the readiness or the validity of the test sample can be determined based on identifying whether a first visual indicia is displayed in a particular area (e.g., where line 2916 is shown in FIG. 29) in the first holding area (e.g., area 2915A). An example of such first visual indicia can be a line displayed in a certain designated area on a test strip, such as shown in FIG. 29 as red line 2916. The red line 2916 may be used to as a quality control means, which can indicate that the test is valid or that the result is ready. Additionally, the first hold area 2915A may include another area (e.g., where line 2917 is shown in FIG. 29) that is to display a second visual indicia representing a test result with respect to a property of the biological specimen. An example of such second visual indicia can be a line displayed in another certain designated area on the test strip, such as shown in FIG. 29 as red line 2917.

In some embodiments, the test equipment can perform an action in response to a determination that the biological specimen is not ready. In some examples, the action to be performed by the processor includes implementing a timer having a time duration that is determined by the analytic processes to be performed. In some other examples, the test equipment further includes a moving mechanism, and the processor in the test equipment can utilize the moving mechanism to apply a mechanical force to the carrier for increasing the readiness of the biological specimen. More detail of the actions and mechanisms that can be implemented in the test equipment are introduced below with respect to FIGS. 25 and 26.

The locations of the magnifying components (e.g., magnifying component of the camera module or magnifying component of the test strips) and locations of the light source(s) can be adjusted or selected depending on the requirements of various types of analyte analysis. In variations, the camera modules can have adjustable magnifying ratios. In at least some of these examples, the processor is further configured to adjust a magnifying ratio of at least one of the two camera modules based on which analytic process that the processor is currently configured to perform. As introduced above, when the biological specimen includes sperm, the test equipment can configure suitable camera modules (e.g., the second camera module 2230B) to reach a different magnifying ratio for determining a motility of the sperm and a morphology of the sperm.

Figure 23:
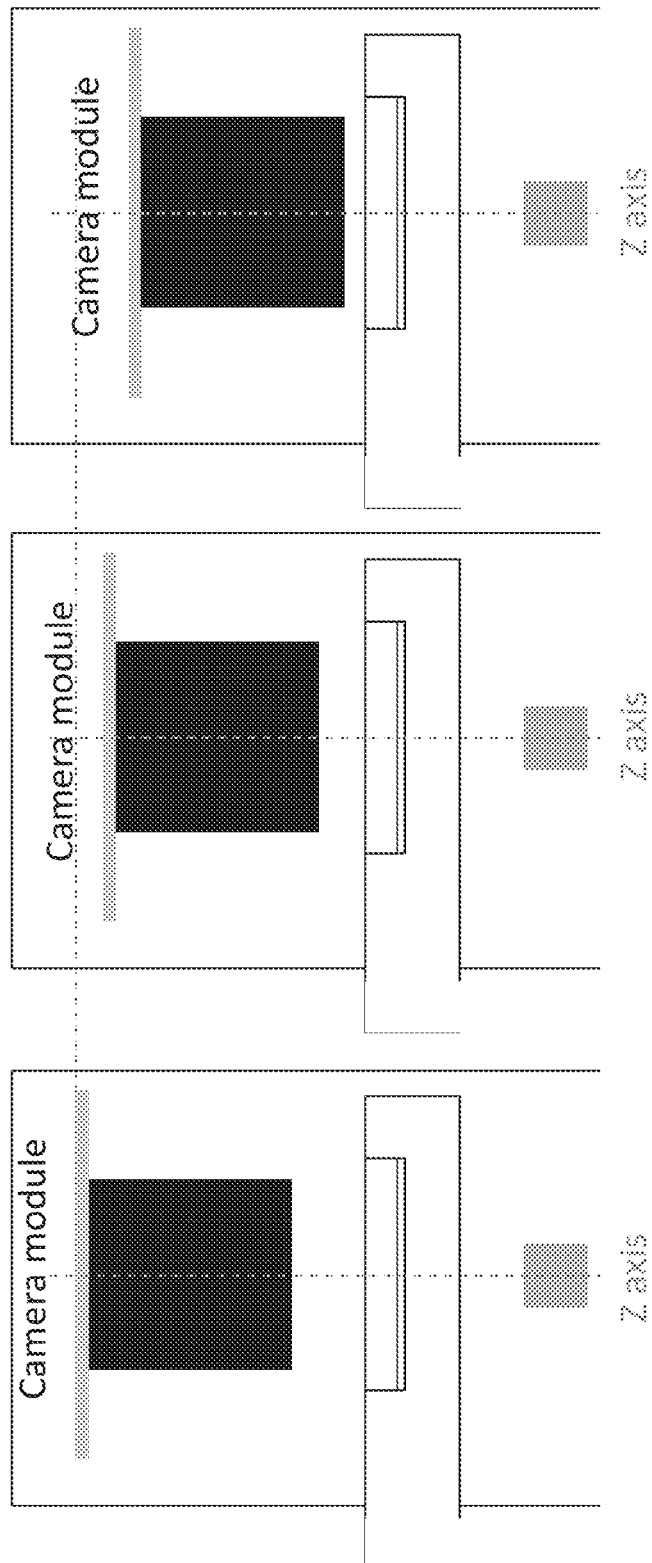
FIG. 23 is schematic diagram of components of a testing equipment having an autofocus function.

Note that an optimal distance between the camera module and the magnifying component may have a low margin of error. For example, even a slight deviation of 0.01 mm from the optimal distance can prevent the camera module to capture a clear image of the specimen holding area. In order to fine tune the distance between the camera module and the magnifying component, the testing equipment can include an autofocus (AF) function. An autofocus function is function that automatically adjusts an optical system (e.g., adjusts distances between components of the optical system) so that the object being imaged (e.g., semen) is within the focal plane of the optical system. At least one or more embodiments also provide a mechanical focusing mechanism, controllable by the processor, to cause at least one of the two camera modules to focus on a respective holding area. The mechanical focusing mechanism is discussed in more detail below with respect to FIGS. 23 and 24. The mechanical focusing mechanism can be controllable to adjust a position of a lens in the at least one of the two camera modules (e.g., such as generally shown in FIG. 23). Additionally or alternatively, the mechanical focusing mechanism can be controllable to adjust a position of the carrier (e.g., such as generally shown in FIG. 24).

FIG. 23 is schematic diagram of components of a testing equipment having an autofocus function. As shown in FIG. 23, the testing equipment can move the camera module upward or downward along the Z-axis (e.g., by a motorized rail, an ultrasonic motor drive, or a stepping motor). By adjusting the vertical position of the camera module, the testing equipment can adjust the distance between the camera module and the magnifying component.

Figure 24:
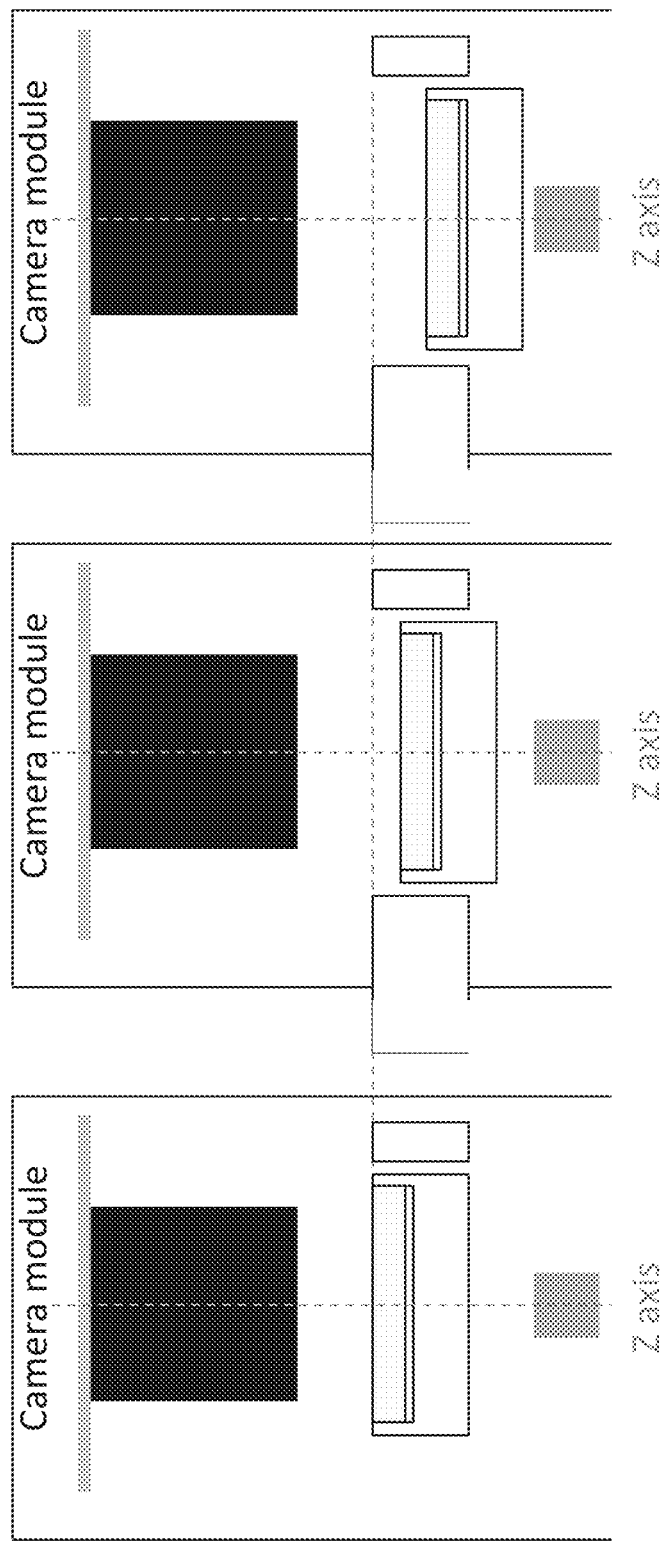
FIG. 24 is schematic diagram of components of another testing equipment having an autofocus function.

FIG. 24 is schematic diagram of components of another testing equipment having an autofocus function. As shown in FIG. 24, the testing equipment can move the test strip device upward or downward along the Z-axis. By adjusting the vertical position of the test strip device, the testing equipment can adjust the distance between the camera module and the magnifying component.

During the autofocus operation as illustrated in FIG. 23 or 24, the camera module and the supplemental lens are kept as a single module. In other words, the distance between the camera module and the supplemental lens remains unchanged during the autofocus operation as illustrated in FIG. 23 or 24.

Figure 25:
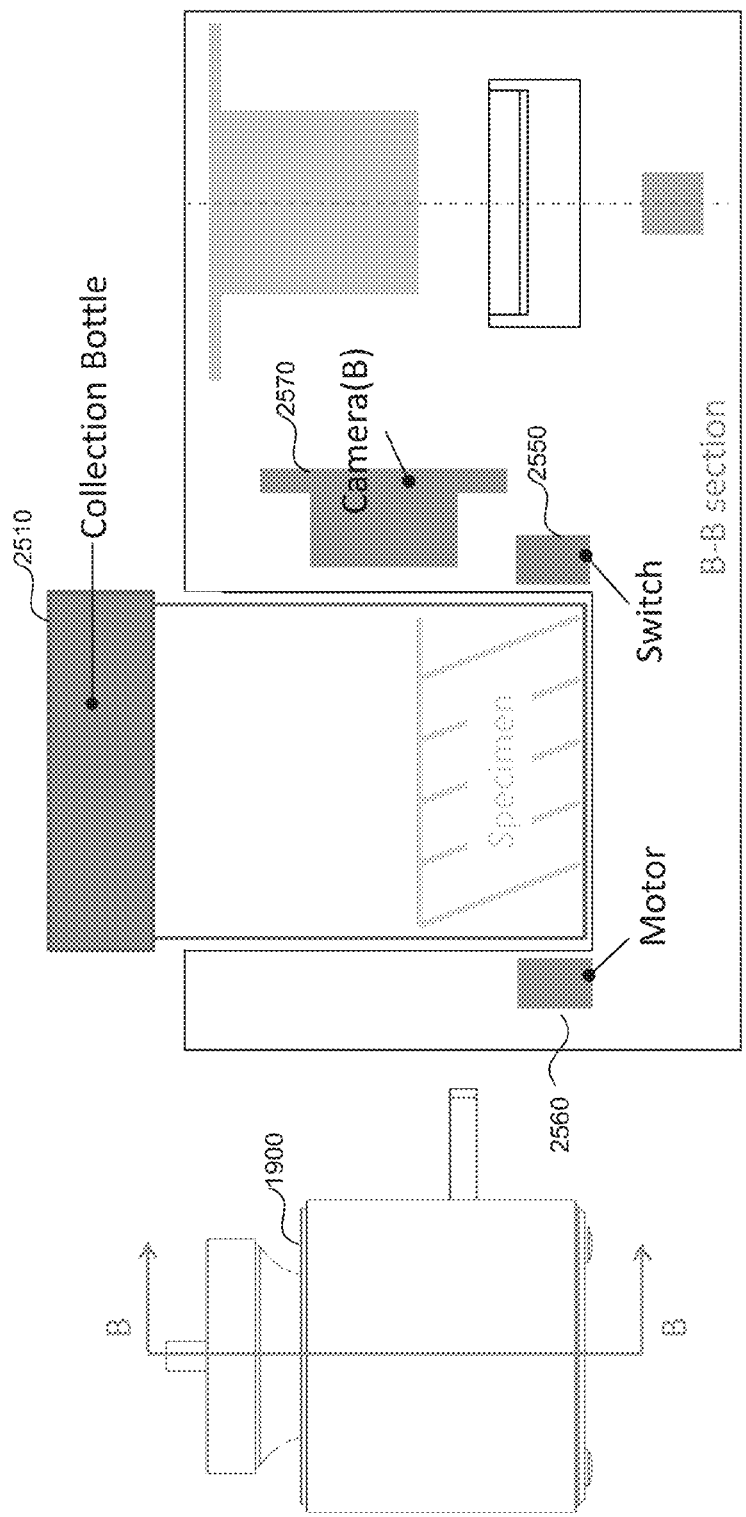
FIG. 25 is a schematic diagram of a testing equipment including a switch and a motor.

FIG. 25 is a schematic diagram of a testing equipment including a switch and a motor. The B-B cross-section of the testing equipment 1900 in FIG. 25 shows various components of the testing equipment. The testing equipment 1900 includes a switch 2550 to detect a collection bottle 2510 being inserted into the testing equipment 1900. When the collection bottle 2510 is inserted, the switch 2550 is activated. The testing equipment 1900 then is notified of the collection bottle 2510 through the switch 2550. Based on the time period for which the switch 2550 is being activated, the testing equipment can determine the time period for which the collection bottle 2510 stays inserted.

The testing equipment 1900 further includes a motor 2560 for shaking, vibrating, or rotating the collection bottle 2510 in order to mix the specimen in the collection bottle 2510. The testing equipment 1900 can include a camera 2570 to determine whether the specimen already liquefies based on captured images of the specimen in the collection bottle 2510.

Figure 26:
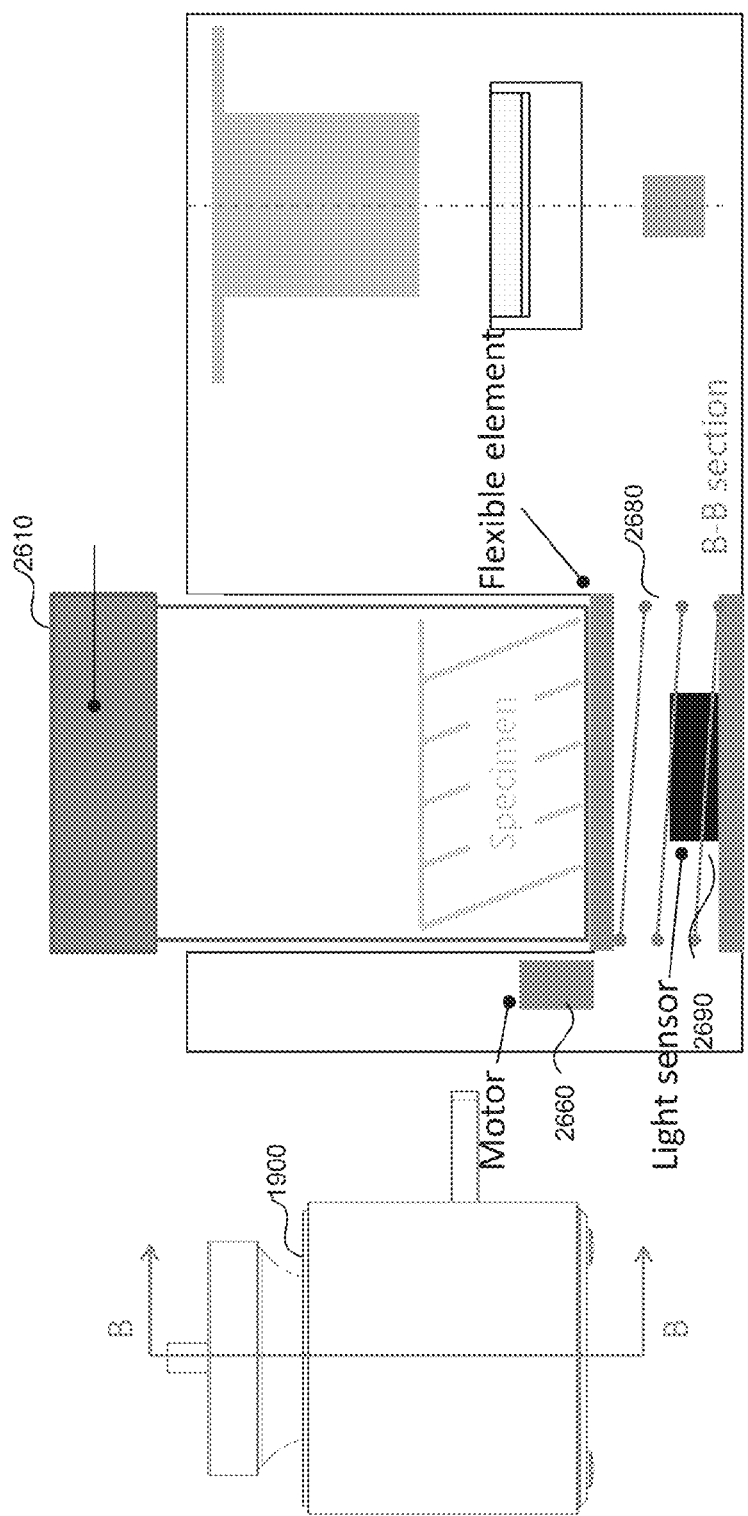
FIG. 26 is a schematic diagram of a testing equipment including a flexible element.

FIG. 26 is a schematic diagram of a testing equipment including a flexible element. The B-B cross-section of the testing equipment 1900 in FIG. 26 shows various components of the testing equipment. The testing equipment 1900 includes a moving element 2680 (e.g. elastic component) at the bottom of the slot for accommodating the collection bottle 2610 in a moving manner. For example, the moving element 2680 can include a spring that can resume its normal shape spontaneously after contraction or distortion. When the collection bottle 2610 is inserted into the slot, the moving element 2680 is compressed. A light sensor 2690 (or other types of distance sensor) is responsible for detecting the distance between the light sensor 2690 and the bottom of the collection bottle 2610. Based on the distance between the light sensor 2690 and the bottom of the collection bottle 2610, the testing equipment 1900 can determine the weight or the volume of the specimen contained in the collection bottle 2610. For example, the distance between the light sensor 2690 and the bottom of the collection bottle 2610 can be inversely proportional to the weight or the volume of the specimen contained in the collection bottle 2610.

In some other embodiments, the testing equipment 1900 can include a sensor on top of the collection bottle 2610. The sensor can be responsible for detecting a distance between the sensor and a top of the collection bottle 2610. The weight or the volume of the specimen contained in the collection bottle 2610 can be determined based on the distance because the volume or the weight can be, e.g., directly proportional to the distance between the sensor and the top of the collection bottle 2610. In turn, based on the weight or the volume of the specimen, the testing equipment 1900 can determine a time period for waiting for the liquefaction of the specimen in the collection bottle 2610. The testing equipment 1900 further includes a motor 2660 for shaking, vibrating, or rotating the collection bottle 2610 in order to mix the specimen in the collection bottle 2610

In some embodiments, the camera module of the testing equipment can include a light field camera (not shown) that captures intensities as well as directions of the light rays. The light field camera can include an array of micro-lenses in front of an image sensor, or multi-camera arrays to detect the directional information. Using the directional information of the light rays, the camera module can capture clear images at a wide range of the focal planes. Therefore, a testing equipment using a light field camera may not need an autofocus function to fine adjust the distance between the camera module and the magnifying component.

With the above in mind, the apparatus of the present invention is useful for testing male fertility and/or female reproductivity.

The present invention provides a method for testing male fertility using the apparatus of the instant application. The method comprises the steps of: applying a biological specimen from a male subject to a first holding area and a second holding area of a carrier; inserting the carrier into the apparatus; determining the acidity of the sperm from the first analytic process; determining one or more properties of the sperm selected from the group consisting of: concentration of the sperm, motility of the sperm, and morphology of the sperm, from the second analytic process; and analyze the results to determine male fertility.

The present invention also provides a method for testing female reproductive hormones using the apparatus of the present application. The method comprises the steps of: applying a biological specimen from a female subject to a first holding area of a carrier; inserting the carrier into the apparatus; and determining the concentration level of one or more types of female hormones such as luteinizing hormone (LH), follicle stimulating hormone (FSH), or human chorionic gonadotropin (HCG).

The present invention further provides a method for testing fertility in a couple of a male subject and a female subject. The method comprises the steps of: applying a biological specimen from the male subject to a first holding area and a second holding area of a first carrier; inserting the first carrier into the apparatus; determining the acidity of the sperm from the first analytic process; determining one or more properties of the sperm selected from the group consisting of: concentration of the sperm, motility of the sperm, and morphology of the sperm, from the second analytic process; applying a biological specimen from the female subject to a holding area of a second carrier; inserting the second carrier into the apparatus; determining a concentration level of one or more types of female hormones; and analyzing the results of the male and the female biological specimen.

Figure 27:
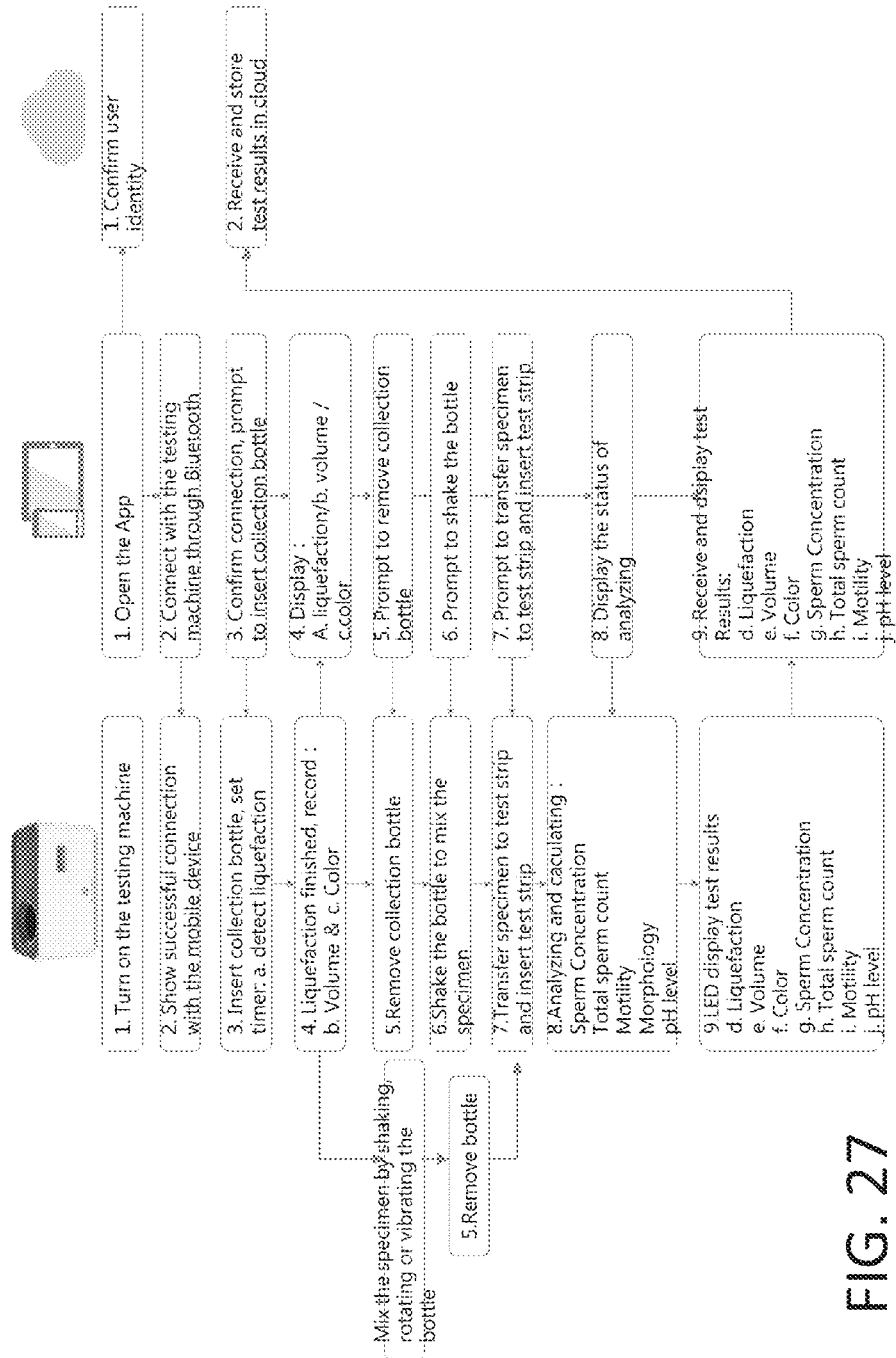
FIG. 27 is a flow chart of a process for analyzing semen specimen for male customers or patients.
Figure 28:
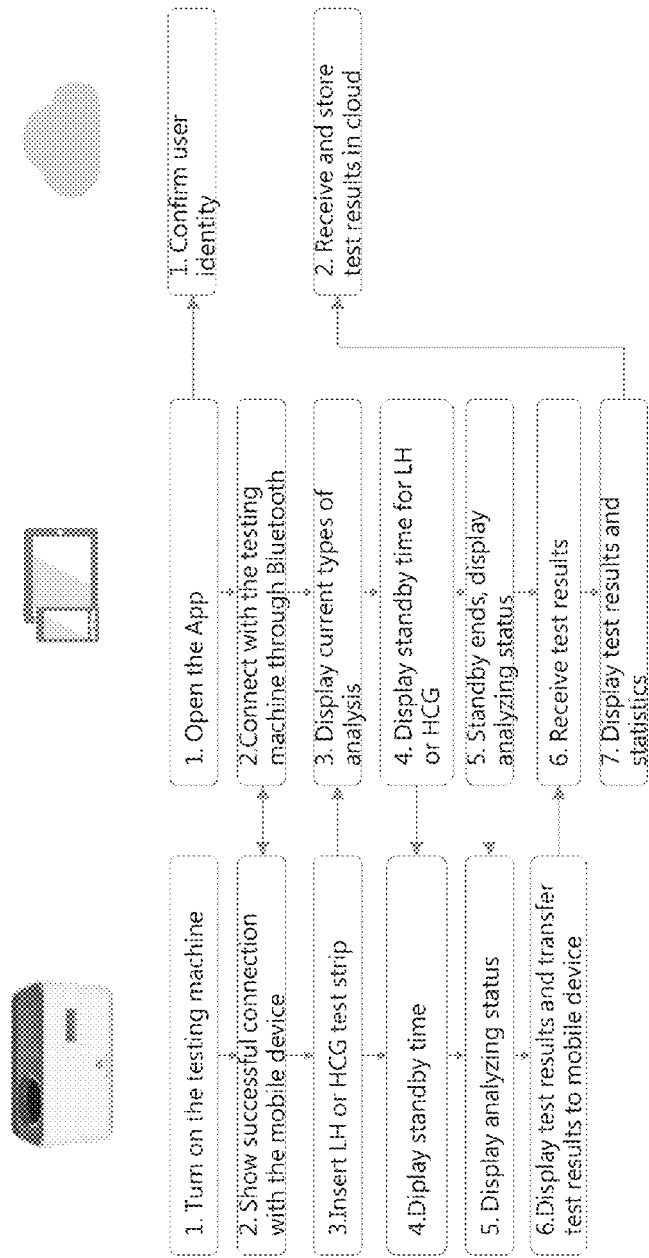
FIG. 28 is a flow chart of a process for analyzing LH or HCG for female customers or patients.

FIG. 27 is a flow chart of a process for analyzing semen specimen for male customers or patients. The system for analyzing semen specimen can include a testing machine (e.g., testing equipment 1900), a mobile device and a cloud server. FIG. 28 is a flow chart of a process for analyzing LH or HCG for female customers or patients. The system for analyzing LH or HCG can include a testing machine (e.g., testing equipment 1900), a mobile device and a cloud server. The flow charts of FIGS. 27 and 28 show steps performed by the testing machine, the mobile device and the cloud server and information being transferred among the testing machine, the mobile device and the cloud server.

In some embodiments, a method for testing sperms comprises steps of: obtaining the device for testing biological specimen; applying a sperm specimen to the specimen holding area, recording a video or an image of the sperm specimen; determining the sperm count of the sperm specimen based on the at least one frame of the recorded video or the recorded image; and determining the sperm motility of the sperm specimen based on the recorded video or the recorded image.

In a related embodiment, the method further comprises: waiting for a pre-determined time period for liquefaction of the sperm specimen before applying the sperm specimen to the specimen holding area.

In another related embodiment, the method further comprises: placing a mobile device including a camera component on top of the device such that the camera component is aligned with the magnifying component and the specimen holding area; and receiving by the mobile device light signal from the sperm specimen in the specimen holding area via magnification by the magnifying component.

In yet another related embodiment, the method further comprises: illuminating the specimen holding area by a lateral illumination device disposed on a side of the carrier of the device or a vertical illumination device disposed on top of or below the carrier of the device.

In still another related embodiment, the method further comprises: guiding light beams from the lateral illumination device throughout the carrier made of a transparent or translucent material; and reflecting the light beams to the specimen holding area by a plurality of light reflecting patterns included in the carrier.

In yet another related embodiment, the method further comprises: inserting the disposable testing device into a base, the base including a camera component for recording the video of the sperm specimen, or a form-fitting frame for securing a mobile device that includes a camera component for recording the video of the sperm specimen.

In still another related embodiment, the method further comprises: extracting at least one frame from the recorded video of the biological specimen; identifying a plurality of sperms from the at least one frame; and calculating the sperm count based on a number of identified sperms and an area recorded by the at least one frame.

In yet another related embodiment, the method further comprises: analyzing shapes of the identified sperms; and determining a morphology level based on the shapes of the identified sperms.

In still another related embodiment, the method further comprises: extracting a series of video frames from the recorded video of the sperm specimen; identifying a plurality of sperms from the series of video frames; identifying moving traces of the sperms based on the series of video frames; determining moving speeds of the sperms based on the moving traces of the sperms and a time period captured by the series of video frames; and calculating the sperm motility based on the moving speeds of the sperms.

In yet another related embodiment, the method further comprises: further magnifying the video or the image of the sperm specimen through a magnifying lens.

In some embodiments, a method for testing sperms using the system for testing biological specimen, comprises: inserting the device into the base component; recording a video of the sperm specimen in the specimen holding area by the mobile device, the mobile device being secured in the form-fitting frame of the base component; determining a sperm count of the sperm specimen based on the at least one frame of the recorded video; and determining a sperm motility of the sperm specimen based on the recorded video.

In a related embodiment, the method further comprises: further magnifying the video of the sperm specimen through a magnifying lens.

In some embodiments, a system for testing biological specimen comprises a disposable device for testing biological specimen and a base component. The disposable device includes a sample carrier including a specimen holding area, and a detachable cover placed on top of the specimen holding area. The base component includes an insertion port for inserting the disposable device into the base component, and a camera component for capturing the image of the specimen holding area, the camera component including an image sensor and an optical lens module. In a related embodiment, the optical lens module can have a linear magnification ratio of at least 0.1.

Although some of the embodiments disclosed herein apply the disclosed technology to sperm test, a person having ordinary skill in the art readily appreciates that the disclosed technology can be applied to test various types of biological specimen, such as semen, urine, synovial joint fluid, epidermis tissues or cells, tumour cells, water sample, etc.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An apparatus for testing biological specimen, the apparatus comprising:
   a casing including an opening;
   a receiving mechanism to receive a carrier inserted through said opening, wherein the carrier includes a first holding area and a second holding area, wherein the first and second holding areas carry or have been exposed to the biological specimen;
   two camera modules, including a first camera module arranged to capture one or more images of the first holding area, and a second camera module arranged to capture one or more images of the second holding area; and
   a main circuit board carrying a processor that is configured to (1) utilize the first camera module to identify a shape of the first holding area on the carrier by performing a first set of analytic processes on the captured images of the first holding area, and (2) select, based on the shape of the first holding area, and perform a second set of analytic processes different from the first analytic processes on the captured images of the second holding area, and to determine an outcome with regard to the biological specimen based on results from both the first and the second analytic processes,
   wherein said receiving mechanism, said first and second camera modules, and said main circuit board are all enclosed within the casing.

2. The apparatus of claim 1, wherein, when the processor identifies the first holding area being in a first shape, indicating that the biological specimen includes sperm from a male subject, the processor is configured to determine one or more properties of the sperm, including: a concentration of the sperm, a motility of the sperm, and/or a morphology of the sperm.

3. The apparatus of claim 2, wherein the determination of the one or more properties of the sperm is performed by using the second camera module.

4. The apparatus of claim 3, wherein the processor is further to determine at least one additional property of the sperm by using the first camera module.

5. The apparatus of claim 4, wherein the at least one additional property includes an acidity of the sperm.

6. The apparatus of claim 5, wherein the carrier includes a pH indicator in the first holding area to represent the acidity of the sperm with colors.

7. The apparatus of claim 2, wherein, when the processor identifies the first holding area being in a second shape, indicating that the biological specimen includes urine from a female subject, the processor is configured to determine one or more properties of the urine, including: an LH level, an FSH level, and/or an HCG level.

8. The apparatus of claim 7, wherein the determination of the one or more properties of the urine is performed by using the first camera module.

9. The apparatus of claim 8, wherein the carrier includes an LH indicator, an FSH indicator, and/or an HCG indicator in the first holding area.

10. The apparatus of claim 1, wherein the first camera module has a lower magnifying ratio and/or a lower camera resolution than the second camera module.

11. The apparatus of claim 1, wherein the shape of the first holding area identifies a gender information of the biological specimen.

12. The apparatus of claim 1, wherein, in response to the shape of the first holding area being a first shape, the set of analytic processes selected by the processor is to determine a fertility with regard to reproductive cells of a first gender.

13. The apparatus of claim 12, wherein, in response to the shape of the first holding area being a second shape, the set of analytic processes selected by the processor is to determine a fertility with regard to reproductive cells of a second gender different than the first gender.

14. The apparatus of claim 1, further comprising:
a display enclosed within the casing,
wherein the processor is configured to display the determined outcome on the display after the outcome becomes available.

15. The apparatus of claim 1, further comprising:
a communication module enclosed within the casing,
wherein the processor is configured to transmit, via the communication module, the one or more images and/or the determined outcome to a device separate from the apparatus.

16. The apparatus of claim 1, further comprising:
a light source enclosed inside the casing and arranged to illuminate the biological specimen for at least one of the camera modules,
wherein the processor is configured to control the light source based on which analytic process that the processor is currently configured to perform.

17. The apparatus of claim 16, further comprising:
a light collimator for collimating light beams emitted from the light source to at least one of the holding areas; and
an annular diaphragm between the light source and the light collimator for forming a hollow cone of light beams that travels through the light collimator and then reaches the specimen holding area.

18. The apparatus of claim 17, further comprising:
a phase plate between the specimen holding area and at least one of the camera modules for phase-shifting light rays reflected from the specimen holding area.

19. The apparatus of claim 1, wherein the processor is operable to receive an instruction from a user, and to perform a select number of the automated analytic processes based on the instruction.

20. The apparatus of claim 1, wherein the processor is configured to utilize at least one of the two camera modules, or another sensor, to determine a readiness or a validity of the biological specimen before performing the analytic processes.

21. The apparatus of claim 20, wherein the readiness or the validity is determined based on identifying whether a first visual indicia is displayed in a particular area in the first holding area.

22. The apparatus of claim 21, wherein the first hold area includes another area that is to display a second visual indicia representing a test result with respect to a property of the biological specimen.

23. The apparatus of claim 20, wherein the processor is configured to perform an action in response to a determination that the biological specimen is not ready.

24. The apparatus of claim 23, wherein the action to be performed by the processor includes implementing a timer having a time duration that is determined by the analytic processes to be performed.

25. The apparatus of claim 23, further comprising:
a moving mechanism enclosed in the casing,
wherein the action to be performed by the processor includes utilizing the moving mechanism to apply a mechanical force to the carrier for increasing the readiness of the biological specimen.

26. The apparatus of claim 1, further comprising:
a mechanical focusing mechanism, controllable by the processor, to cause at least one of the two camera modules to focus on a respective holding area.

27. The apparatus of claim 26, wherein the mechanical focusing mechanism is controllable to adjust a position of a lens in the at least one of the two camera modules and/or a position of the carrier.

28. The apparatus of claim 1, wherein the biological specimen includes sperm, and wherein the processor is configured to (1) determine a concentration of the sperm and/or a morphology of the sperm based on a single image from the captured images, and (2) determine a motility of the sperm based on two or more images from the captured images.

29. The apparatus of claim 1, wherein the processor is further configured to adjust a magnifying ratio of at least one of the two camera modules based on which analytic process that the processor is currently configured to perform.

30. The apparatus of claim 29, wherein the biological specimen includes sperm, and wherein the processor is to configure a different magnifying ratio for determining a motility of the sperm and a morphology of the sperm.

31. The apparatus of claim 1, wherein the processor is further configured to determine a biochemical property of the biological specimen based on a color of a region in the one or more images of the first or second holding area.

32. The apparatus of claim 1, further comprising a battery compartment enclosed within the casing, the battery compartment configured to receive a battery that powers the apparatus.

33. The apparatus of claim 1, wherein a form factor of the casing is smaller than 27,000 cubic centimeters.

* * * * *